(12) United States Patent
Cheeseman et al.

(10) Patent No.: US 8,501,154 B2
(45) Date of Patent: Aug. 6, 2013

(54) FLUORINATED FRUCTOSE DERIVATIVES FOR PET IMAGING

(71) Applicant: The Governors of the University of Alberta, Edmonton (CA)

(72) Inventors: Chris Cheeseman, Edmonton (CA); Frederick West, Edmonton (CA); Tina Grant, Edmonton (CA); Brendan Trayner, Edmonton (CA); John Mercer, Edmonton (CA); Andrei Manolescu, Edmonton (CA)

(73) Assignee: The Governors of the University of Alberta, Calgary, Alberta (CA)

( * ) Notice: Subject to any disclaimer, the term of this patent is extended or adjusted under 35 U.S.C. 154(b) by 0 days.

(21) Appl. No.: 13/622,599

(22) Filed: Sep. 19, 2012

(65) Prior Publication Data

US 2013/0078184 A1   Mar. 28, 2013

Related U.S. Application Data

(62) Division of application No. 12/467,052, filed on May 15, 2009, now Pat. No. 8,293,208.

(51) Int. Cl.
*A61K 51/00* (2006.01)
*A61M 36/14* (2006.01)

(52) U.S. Cl.
USPC ....... 424/1.73; 424/1.11; 424/1.85; 424/1.89; 424/1.61; 536/1.22

(58) Field of Classification Search
None
See application file for complete search history.

*Primary Examiner* — Michael G Hartley
*Assistant Examiner* — Sean R Donohue
(74) *Attorney, Agent, or Firm* — Bennett Jones LLP

(57) ABSTRACT

The present invention is directed to fructose-based radiopharmaceuticals, pharmaceutical compositions comprising same, precursors and methods for preparing same, and methods of using same for diagnostic imaging of cancer cells and non-imaging tracer studies.

6 Claims, 9 Drawing Sheets

FLUORINATED FRUCTOSE DERIVATIVES FOR PET IMAGING

CROSS REFERENCE TO RELATED APPLICATION

This application is a divisional application of U.S. patent application Ser. No. 12/467,052 filed on May 15, 2009 entitled "Fluorinated Fructose Derivatives for Pet Imaging", the contents of which are incorporated herein by reference.

FIELD OF THE INVENTION

This invention relates to fructose-based radiopharmaceuticals, pharmaceutical compositions comprising same, precursors and methods for preparing same, and methods of using same for diagnostic imaging of cancer cells and non-imaging tracer studies.

BACKGROUND OF THE INVENTION

Positron emission tomography (PET) is a nuclear medicine imaging technique for studying metabolic and physiological processes and tissue microenvironments, and diagnosing or treating diseases including cancer, heart disease and brain abnormalities. PET uses non-toxic radiopharmaceutical agents formed from biologically relevant molecules labelled with positron-emitting radionuclides. Following administration to the body, the radiopharmaceutical agent localizes within the tissue of interest. When the isotope decays, it emits a positron which then annihilates with an electron of a nearby atom, producing gamma rays. The PET scanner detects gamma ray photons, thereby producing an image of the tissue for interpretation by a radiologist.

Due to its emission of positrons and half-life of 110 minutes, fluorine-18 ($^{18}F$) is a widely accepted radionuclide for PET, and is commonly synthesized into fluorodeoxyglucose (FDG) to form 2-deoxy-2-[$^{18}F$] fluoro-D-glucose ($^{18}F$-FDG). FDG is a sugar compound which is processed by growing cancer cells, the brain, and cardiac muscles. Transport of sugar through cell membranes requires transport proteins known as GLUTs. Imaging tumours with PET traditionally uses [$^{18}F$]-FDG as the imaging agent to take advantage of the characteristic overexpression of facilitated hexose transporter isoform GLUT1 (SLC2A1) in certain cancerous cells. [$^{18}F$]-FDG is subsequently trapped and accumulated within the cells as a result of phosphorylation at the 6-position by hexokinase II, an enzyme which is overexpressed in many cancers (Santiago et al., 2006; Buerkle, 2008; Hamberg et al., 1994; and Mavi et al., 2006). [$^{18}F$]-FDG has been used to evaluate metastatic and recurring cancer, and to detect the primary disease (Eubank et al., 2005; Kumar et al., 2004; Santiago et al., 2006; Schirmer et al., 2003; Weir et al., 2005).

In breast cancer, it is widely recognized that the Class II hexose transporter GLUT5, which can readily move fructose across the cell membrane, is more highly expressed in transformed breast tissue compared to normal, untransformed tissue (Zamora-Leon et al., 1996; Godoy et al., 2006; Ponten et al., 2008). Not only is GLUT5 overexpressed, but the Class I glucose/fructose-transporting isoform GLUT2 is also overexpressed in cancerous breast tissue, which likely contributes to increased fructose uptake in these tumoural cells. The increased expression of both GLUT5 and GLUT2 may be indicative of the cells' broadening their substrate preference to compensate for an increased demand for metabolic fuel. This theory is supported by the observed ability of anti-sense oglionucleotide induced knockdown of GLUT5 to decrease the proliferation of breast cancer cells in vivo (Chan et al., 2004). The knowledge that breast cancers exhibit overexpression of GLUT5 and GLUT2 suggests that an [$^{18}F$]-labelled fructose analogue may have potential for the imaging and diagnosis of these tumours (Zamora-Leon et al., 1996; Godoy et al., 2006; and Haradahira et al., 1995). [$^{18}F$]-FDG is inefficiently transported by GLUT-2 and not at all by GLUT-5, and thus will be poorly taken up by breast cancers that overexpress these transporters over GLUT-1. Radiolabelled fructose analogues which are targeted to the Class II fructose-transporting GLUT5 and the Class I glucose/fructose-transporting GLUT2 may reveal a new avenue for improved imaging of breast and other cancers with similar GLUT expression profiles.

[$^{18}F$]-FDG-PET is ineffective in the detection of small tumours and more differentiated sub-types such as tubular carcinomas or lobular carcinomas (Kumar et al., 2004; Buck et al., 2002; Crippa et al., 1998). $^{18}F$-FDG also accumulates in areas of inflammation, making it difficult to distinguish between cancerous and inflamed tissues upon imaging. Macrophages and other immune cells have been implicated in the generation of false positives when using [$^{18}F$]-FDG-PET due to increased uptake of large quantities of glucose and [$^{18}F$]-FDG by these cells (Buck et al., 2002; Fu et al., 2004). Macrophages are strongly associated with tumour sites and contribute a large percentage of the total tumoural cell count, especially after treatment with chemotherapeutics when macrophage numbers actually increase due to the destruction of tumoural cells. This phenomenon can be responsible for an increase in the observed [$^{18}F$]-FDG uptake by PET, generating false-positives in images used to monitor treatment efficacy (Schirmer et al., 2003; Kubota et al., 1994).

The stages for PET imaging generally involve radionuclide production in a cyclotron, synthesis of a precursor, radiolabelling in a radiotracer laboratory, purification, administration to a subject, a PET scan, and image analysis and evaluation. PET chemistry with $^{18}F$ must be completed rapidly preferably within an hour to provide sufficient radioactive tracer for a PET scan. The preparation of imaging radiopharmaceuticals using $^{18}F$ as a PET radionuclide requires rapid high yield reactions which can be accomplished by the preparation of suitable precursor molecules. Preparation of suitable precursors can be difficult and time consuming.

There is a need for methods and reagents for facilitating the efficient syntheses of fructose-based radiopharmaceuticals for PET. Further, fructose-based radiopharmaceuticals which improve contrast between cancerous and inflamed tissues, and enhance diagnostic imaging of breast cancer cells are desirable.

SUMMARY OF THE INVENTION

The present invention is directed to fructose-based radiopharmaceuticals, pharmaceutical compositions comprising same, precursors and methods for preparing same, and methods of using same for diagnostic imaging of cancer cells and non-imaging tracer studies.

In one aspect, the invention comprises a radiopharmaceutical of the formula:

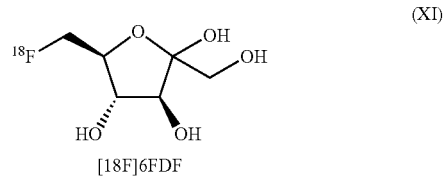 [SMILES: OCC1(O)O[C@H](C[18F])[C@@H](O)[C@@H]1O]

[18F]6FDF

In one aspect, the invention comprises a compound of the formula:

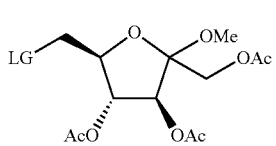
(X)

wherein LG represents a leaving group. In one embodiment, the leaving group is a trifluoromethanesulfonate (triflate), chloride, bromide, iodide, 4-nitrophenylsulfonate (nosylate), 4-methylphenylsulfonate (tosylate), or phenylsulfonate group.

In one aspect, the invention comprises a method of preparing the radiopharmaceutical of formula (XI) comprising: reacting the compound of formula (X) with a radioactive fluorinated complex to displace the leaving group to yield the radiopharmaceutical of formula (XI). In one embodiment, the compound of formula (X) is reacted with $[^{18}F]FK\text{-}K_{222}$ activated complex in acetonitrile at 85° C., followed by addition of hydrochloric acid at 110° C.

In one aspect, the invention comprises use of a compound of the formula (X) in the preparation of the compound of formula (XI).

In one aspect, the invention comprises a pharmaceutical composition comprising an effective amount of the compound of formula (XI) in combination with one or more pharmaceutically acceptable carriers.

In one aspect, the invention comprises a method for diagnosing or treating cancer in a subject comprising administering an effective amount of a radiopharmaceutical to the subject, and imaging cancer tissue using positron emission tomography, wherein the radiopharmaceutical is the compound of formula (XI), and is capable of being retained within cancer tissue sufficient to emit positrons for detection by positron emission tomography. In one embodiment, the cancer is selected from a cancer of the brain, lung, breast, pancreas, kidney, colon, rectum, ovary, prostate, head, neck, thyroid, bladder, bone, endometrium, testicular cancer, gastric cancer, or neuroblastoma.

In one aspect, the invention comprises a method for monitoring cancer in a subject comprising: administering an effective amount of a radiopharmaceutical to a subject undergoing medical treatment for cancer; imaging cancer tissue using positron emission tomography; and comparing the quantity or distribution of the radiopharmaceutical present in the subject with a control quantity or distribution indicative of the effectiveness of the medical treatment, wherein the radiopharmaceutical is the compound of formula (XI), and is capable of being retained within cancer tissue sufficient to emit positrons for detection by positron emission tomography. In one embodiment, the cancer is selected from a cancer of the brain, lung, breast, pancreas, kidney, colon, rectum, ovary, prostate, head, neck, thyroid, bladder, bone, endometrium, testicular cancer, gastric cancer, or neuroblastoma.

In one aspect, the invention comprises a method of preparing 6-deoxy-6-fluoro-D-fructose comprising: treating methyl 1,3,4,-tri-O-acetyl-6-deoxy-6-fluoro-α/β-D-fructofuranoside (VII) with methanol, followed by NaOMe, to produce a residue (VIII); and reacting the residue (VIII) with 1,4-dioxane, followed by hydrochloric acid, to produce 6-deoxy-6-fluoro-D-fructose (IX). In one embodiment, the method comprises treating D-fructose (I) with methanol and sulfuric acid to produce α- and β-anomers of methylfructofuranosides (II, III). In one embodiment, the method comprises treating the α- and β-anomers of methylfructofuranosides (II, III) with pyridine and tert-butylchlorodimethylsilane to produce methyl 6-O-(tert-butyldimethylsilyl)-α/β-D-fructofuranosides (IV). In one embodiment, the method comprises treating the methyl 6-O-(tert-butyldimethylsilyl)-α/β-D-fructofuranosides (IV) with pyridine and acetic anhydride to produce methyl 1,3,4-tri-O-acetyl-6-O-(tert-butyldimethylsilyl)-β/β-D-fructofuranosides (V). In one embodiment, the method comprises treating the methyl 1,3,4-tri-O-acetyl-6-O-(tert-butyl dimethylsilyl)-α/β-D-fructofuranosides (V) with methylene chloride and trifluoroacetic acid to produce methyl 1,3,4-tri-O-acetyl-6-deoxy-6-fluoro-α/β-D-fructofuranosides (VI). In one embodiment, the method comprises treating the methyl 1,3,4-tri-O-acetyl-6-deoxy-6-fluoro-α/β-D-fructofuranosides (VI) with methylene chloride, followed by pyridine and triflic anhydride, to yield a 6-O-triflyl product. In one embodiment, the method comprises treating the 6-O-triflyl product with tert-amyl alcohol and cesium fluoride to produce methyl 1,3,4-tri-O-acetyl-6-deoxy-6-fluoro-α/β-D-fructofuranoside (VII).

In another aspect, the invention comprises a method of determining hexose uptake by a cell using the compound of formula (IX).

In another aspect, the invention comprises a method of treating cancer comprising use of the compound of formula (IX) to outcompete cancer cells for fructose in GLUT-mediated hexose uptake.

In yet another aspect, the invention comprises a method of determining hexose uptake by a cell using $[^{14}C]$-6-deoxy-6-fluoro-D-fructose.

BRIEF DESCRIPTION OF THE DRAWINGS

The invention will now be described by way of an exemplary embodiment with reference to the accompanying simplified, diagrammatic, not-to-scale drawings.

DETAILED DESCRIPTION OF PREFERRED EMBODIMENTS

Figure 1:
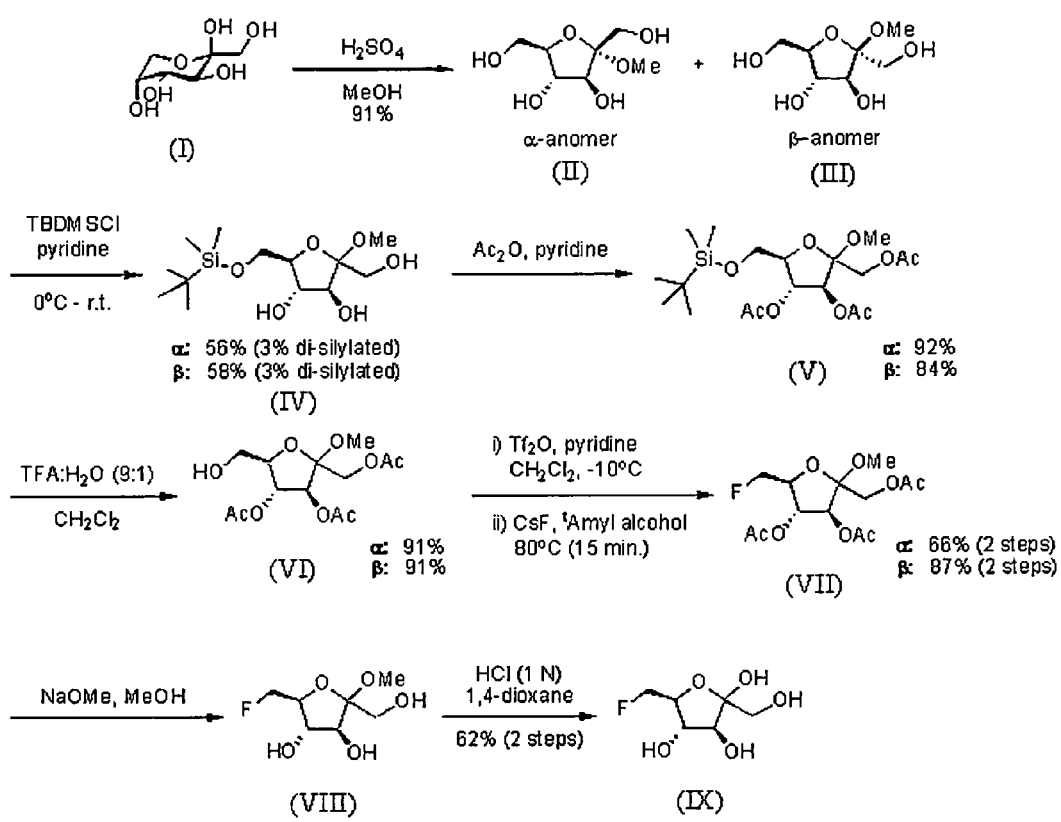
FIG. 1 shows one embodiment of a synthesis of 6-deoxy-6-fluoro-D-fructose according to the present invention.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

To facilitate understanding of the invention, the following definitions are provided:

As used herein, the term "biocompatible" means generating no significant undesirable host response for the intended utility. Most preferably, biocompatible materials are non-toxic for the intended utility. Thus, for human utility, biocompatible is most preferably non-toxic and otherwise non-damaging to humans or human tissues.

As used herein, the term "carrier" means a suitable vehicle which is biocompatible and pharmaceutically acceptable, including for instance, liquid diluents which are suitable for administration.

As used herein, the term "effective amount" means any amount of a formulation of a radiopharmaceutical useful for diagnostic imaging of cancer cells upon administration.

As used herein, the term "fructose-based" means a radiopharmaceutical which includes fructose, analogs or derivatives thereof.

As used herein, the term "pharmaceutically acceptable" means a substance which does not significantly interfere with the effectiveness of the radiopharmaceutical, and which has an acceptable toxic profile for the host to which it is administered.

As used herein, the term "subject" means a human or other mammalian subject. Non-human subjects may include primates, livestock animals (e.g., sheep, cows, horses, goats, pigs) domestic companion animals (e.g., cats, dogs) laboratory test animals (e.g., mice, rats, guinea pigs, rabbits) or captive wild animals.

The present invention is directed to fructose-based radiopharmaceuticals, pharmaceutical compositions comprising same, precursors and methods for preparing same, and methods of using same for diagnostic imaging of cancer cells and non-imaging tracer studies.

The C1, C2, C4 and C5 positions of the substrate must be available to ensure sufficient transport by GLUT proteins (Haradahita et al., 1995). When designing the fructose-based radiopharmaceutical of the present invention, the placement of the fluorine was addressed since it can have implications with regard to its transport and subsequent metabolism. This fact was exemplified by Haradahita et al. (1995) wherein substitution of [$^{18}$F] at the 1-position of fructose afforded a compound that was taken up into cells, but not specifically localized or trapped in tissues with high fructose metabolism. It also demonstrated that metabolism of the fructose analogue was dramatically influenced by fluorination at C-1, although transport remained unaffected. In a study of high-affinity ligands for GLUT5, substitution at the 6-position is well tolerated by the transporter and, in some instances, can actually increase the molecule's affinity (Holman et al., 2002). An increase in substrate affinity would be a considerable advantage for a fructose analogue that is to be used with PET since, when working with patients, relatively small concentrations of tracer will be injected requiring high affinity transport in vivo to ensure its efficacy as a PET tracer.

The ability of the fructose-based radiopharmaceuticals of the present invention to be retained within tumoural cells once transported inside was addressed. As previously discussed, [$^{18}$F]-FDG FDG is transported into cells and phosphorylated, leading to the accumulation of [$^{18}$F] in the cells for imaging with PET. Fructose analogues can enter cancerous cells and be trapped and accumulated via one of two possible routes involving phosphorylation by hexokinase at the C-6 position or ketohexokinase (fructokinase) at the C-1 position (Levi et al., 2007). Each enzyme possesses a different affinity and reactivity towards fructose, so placement of fluorine at either the C-6 or C-1 position leaves the other positions open for phosphorylation by the other enzyme. Fructose-based radiopharmaceuticals of the present invention may be readily transported by GLUT5 and phosphorylated by fructokinase.

In one embodiment, the fructose-based radiopharmaceutical comprises the compound of formula (XI).

In one aspect, the present invention is directed to processes for preparing radiopharmaceuticals. In one embodiment, the compound of formula (XI) is prepared using the compound of formula (X) as a precursor.

In one aspect, the present invention is directed to a process of preparing 6-deoxy-6-fluoro-D-fructose of the formula (IX) from fructose:

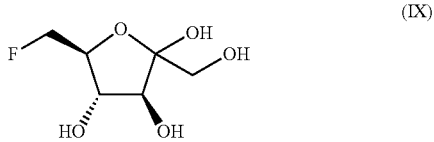 [SMILES: OCC1(O)O[C@H](CF)[C@@H](O)[C@@H]1O]

(IX)

As a starting material, D-fructose is inexpensive and readily available. Briefly, treatment of fructose with acidic methanol affords a mixture of methyl α/β-D-fructofuranosides (II, III) which may be separated using standard silica gel chromatography or, alternatively, carried on as a mixture (FIG. 1). Selective protection of the primary C-6 hydroxyl with tert-butyldimethylchlorosilane (TBDMSCl) in pyridine, followed by global acetylation produces intermediate (V) in moderate yield over the two steps. The silyl protecting group is removed by treatment with aqueous trifluoroacetic acid in dichloromethane to provide intermediate (VI) in 91% (Tatibouet et al., 2000). Compound (VI) is then fluorinated via triflation under standard conditions and immediate treatment with three equivalents of cesium fluoride in refluxing tert-amyl alcohol (Kim et al., 2006). The quick and clean fluoride displacement reaction is useful for installation of [$^{18}$F] for imaging experiments. Standard deprotection of the acetates using sodium methoxide followed by acidic hydrolysis of the methyl fructofuranoside provides 6-deoxy-6-fluoro-D-fructose (IX) as a white solid in 62% (two steps).

As set forth in Examples 1-7, the detailed steps of the process are as follows. D-fructose (I) is used as the starting material to produce α- and β-anomers of methylfructofuranosides (II, III). The α- and β-anomers of methylfructofuranosides (II, III) are treated with TBDMSCl to produce methyl 6-O-(tert-butyldimethylsilyl)-α/β-D-fructofuranosides (IV). The methyl 6-O-(tert-butyldimethylsilyl)-α/β-D-fructofuranosides (IV) are treated with pyridine and acetic anhydride to produce methyl 1,3,4-tri-O-acetyl-6-O-(tert-butyldimethylsilyl)-α/β-D-fructofuranosides (V). The methyl 1,3,4-tri-O-acetyl-6-O-(tert-butyldimethylsilyl)-α/β-D-fructofuranosides (V) are treated with methylene chloride and trifluoroacetic acid to produce methyl 1,3,4-tri-O-acetyl-6-deoxy-6-fluoro-α/β-D-fructofuranosides (VI).

The methyl 1,3,4,-tri-O-acetyl-6-deoxy-6-fluoro-α/β-D-fructofuranosides (VI) are treated with methylene chloride, followed by pyridine and triflic anhydride, to yield a 6-O-triflyl product. This product is then treated with tert-amyl alcohol and cesium fluoride to produce methyl 1,3,4-tri-O-acetyl-6-deoxy-6-fluoro-α/β-D-fructofuranoside (VII). Methyl 1,3,4-tri-O-acetyl-6-deoxy-6-fluoro-α/β-D-fructofuranoside (VII) is treated with methanol, followed by NaOMe, to produce a residue (VIII). The residue is reacted with 1,4-dioxane, followed by hydrochloric acid, to produce 6-deoxy-6-fluoro-D-fructose (IX). In one embodiment, the overall yield is 15%. The structure of 6-deoxy-6-fluoro-D-fructose (IX) is confirmed by examination of one or more spectra including, but not limited to, infrared spectra, mass spectra, proton NMR spectra (500 MHz), and carbon NMR spectra (125 MHz), 6-Deoxy-6-fluoro-D-fructose (IX) is preferably stored in the 6-OH form since it is not stable during prolonged storage.

In one aspect, the invention comprises a method of determining hexose uptake by a cell using the compound of formula (IX).

In one aspect, the invention comprises a method of treating cancer comprising use of the compound of formula (IX) to outcompete cancer cells for fructose in GLUT-mediated hexose uptake.

As described in Example 8, 6-deoxy-6-fluoro-D-fructose was examined for its potential for transport and accumulation in breast cancer cells. Expression analysis of GLUT isoforms was performed on two GLUT5 expressing breast cancer cell lines using Western immunoblotting and immunocytochemistry. Uptake and inhibition studies were undertaken using [$^{14}$C]-labelled hexoses. Transport inhibition studies showed dose dependent inhibition of fructose transport in both cell lines by newly synthesized 6-deoxy-6-fluoro-D-fructose.

Near linear uptake over time of [$^{14}$C]-labelled 6-deoxy-6-fluoro-D-fructose was observed in both cell lines. In one aspect, the invention comprises [$^{14}$C]-6-deoxy-6-fluoro-D-fructose. As described in Example 8, [$^{14}$C]-6-deoxy-6-fluoro-D-fructose was synthesized using the process shown in FIG. 1 with [$^{14}$C]-fructose as the starting material. The synthesis of [$^{14}$C]-6-deoxy-6-fluoro-D-fructose (SA~1 μCi/ml) was accomplished with a 13% overall yield. Only three purification steps were performed to limit unnecessary exposure to the radiolabelled compound. In one aspect, the invention comprises a method of determining hexose uptake by a cell using [$^{14}$C]-6-deoxy-6-fluoro-D-fructose.

The results of the studies described in Example 8 demonstrate the ability of 6-deoxy-6-fluoro-D-fructose to inhibit fructose transport mediated by GLUT2 and GLUT5 with a very low $K_i$ and accumulation of [$^{14}$C]-6-deoxy-6-fluoro-D-fructose in both MCF-7 and MDA-MB-231 cells.

Imaging with [$^{18}$F]-labelled 6-deoxy-6-fluoro-D-fructose may thus improve the monitoring of cancer progression in response to treatment with chemotherapeutic agents, and image resolution with clear distinction of tumoural cells from surrounding inflammation since an [$^{18}$F]-labelled fructose analogue would not be transported into immune cells, which have characteristically low expression of both GLUT2 and GLUT5. Fructose-based PET tracers have the potential to illuminate tumoural cells associated with fructose uptake and metabolism, improving image resolution by eliminating the contribution from immune cells.

It is well known that fructose is a preferred substrate over glucose for certain breast cancer cells which express the fructose transporters, GLUT2 and GLUT5, at higher levels than normal tissue. The C1, C2, C4 and C5 positions of the fructose substrate must be available to ensure sufficient transport by GLUT proteins (Haradahita et al., 1995). In one embodiment, the fluorine is installed at the C3 position of fructose. In one embodiment, the fluorine is installed at the C6 position of fructose.

In the radiopharmaceuticals of the claimed invention, the radionuclide may be any acceptable radionuclide including, but not limited to, fluorine-18, radioactive isotopes of iodine, bromine and chlorine, or others as will be apparent to those skilled in the art. In one embodiment, the radionuclide is $^{18}$-fluorine ($^{18}$F). The incorporation of the selected radionuclide preferably occurs in the final reactions of the overall synthesis, since the half lives of particular radionuclides may be short; for example, the half life of the [$^{18}$F] radionuclide is about 110 minutes. The final reactions are preferably rapid and clean, requiring minimal additional steps or manipulation after incorporation of the radionuclide.

In one aspect, the radiopharmaceutical is [$^{18}$F]-6-deoxy-6-fluoro-D-fructose of the formula:

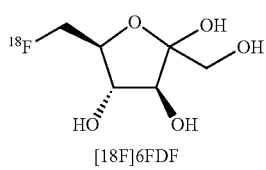

[18F]6FDF (XI)

In one aspect, the invention is directed to a process for preparing [$^{18}$F]-6-deoxy-6-fluoro-D-fructose (XI) using a compound of the formula (X) as the starting material:

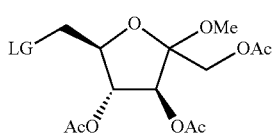

(X)

wherein LG represents a leaving group, which may comprise a trifluoromethanesulfonate (triflate), chloride, bromide, iodide, 4-nitrophenylsulfonate (nosylate), 4-methylphenylsulfonate (tosylate), phenylsulfonate, or other group capable of being replaced by fluorine in a suitable chemical reaction. The term "leaving group" is well understood by those skilled in the art. As set forth in FIG. 2, the compound of formula (X) is reacted with [$^{18}$F]FK-K$_{222}$ activated complex in acetonitrile at 85° C., and hydrochloric acid at 110° C. to yield [$^{18}$F]-6-deoxy-6-fluoro-D-fructose (XI). In one embodiment, the overall yield is 43% using the process of the present invention. In one embodiment, [$^{18}$F]-6-deoxy-6-fluoro-D-fructose is obtained in more than 99% radiochemical purity. In one embodiment, the total synthesis time is about 120 min from the start of the radiofluorination.

Figure 2:
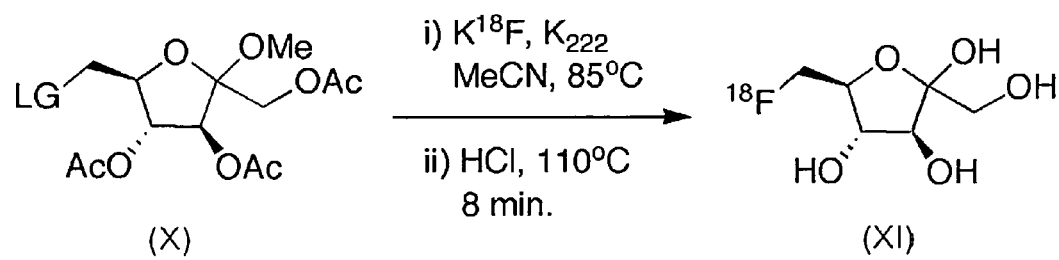
FIG. 2 shows one embodiment of a synthesis of $[^{18}F]$-6-deoxy-6-fluoro-D-fructose according to the present invention.

It will be appreciated by those skilled in the art that [$^{18}$F]-6-deoxy-6-fluoro-D-fructose may be prepared without undue experimentation by methods analogous to those specifically disclosed herein, or by standard automated reaction equipment such as, for example, a Modular-Lab™ (Eckert & Ziegler, Valencia, Calif.), which may be used to conduct the steps shown in FIG. 2. In one embodiment, the method involves transferring 0.659 GBq of 18F in 3 mL water to a QMA cartridge. The activity is then transferred to the first reactor by dilution with 0.8 mL of a standard Kryptofix/K$_2$CO$_3$ solution. The water is removed by co-evaporation with acetonitrile under reduced pressure at 110° C. A solution of methyl 1,3,4-tri-O-acetyl-6-O-triflyl-α/β-D-fructofuranoside (20 mg) in 1.5 mL anhydrous acetonitrile is then added to the first reactor and the solution is heated for 5 min at 85° C. The reaction mixture is then cooled and diluted with 2 mL water. This reaction mixture is then transferred to a Plus tC18™ cartridge, and the aqueous solution collected in a waste vial. The radiolabelled compound is then transferred to the second reactor by dilution with 2 mL acetonitrile, and the solution then concentrated to dryness under reduced pressure at 85° C. To the residue, 1 mL of 2N HCl is added and the reaction mixture is heated to 110° C. for 8 min. The reactor is then cooled and 0.5 mL of 2N NaOH with 1 mL of sat'd NaHCO$_3$ is added. This solution is stirred for 1 min before being passed through a glass wool plug, light C18 cartridge and a neutral alumina cartridge connected in sequence. This method provides the product, 6-deoxy-6-[$^{18}$F]fluoro-D-glucose, in >95% radiochemical purity. Currently, the total synthesis time is 120 min from the start of the radiofluorination and the overall yield is 43% (de).

In one embodiment, [$^{18}$F]-6-deoxy-6-fluoro-D-fructose is further purified using standard techniques including, but not limited to, purification using Sep-Pak™ cartridges (Waters Corp., Milford, Mass.) or the like.

The utility of the radiopharmaceuticals may be confirmed by testing in various ways, including for example, in vitro cell culture assays using human cancer cells including, but not limited to, the MCF-7 and MDA-MB-231 breast cancer cell lines which are responsive to the radiopharmaceuticals. Inhibition of fructose or glucose transport, or uptake may be assessed, as described for instance, in Example 8.

The radiopharmaceuticals may also be evaluated in vivo using murine models. For example, the radiopharmaceuticals may be administered to mice having syngeneic or human tumor xenografts by various routes of administration including, but not limited to, orally, intravenously or intraperitoneally in appropriate dosage forms and fixed dosages. Assessments following treatment of the radiopharmaceuticals may include, but are not limited to, pharmacokinetics, biodistribution, uptake, cancer cell responses, toxicity, histopathology, and host morbidity.

In one aspect, the invention comprises pharmaceutical compositions comprising the radiopharmaceuticals of the present invention in combination with one or more pharmaceutically acceptable carriers. Those skilled in the art are familiar with any pharmaceutically acceptable carrier that would be useful in this regard, and therefore the procedure for making pharmaceutical compositions in accordance with the invention will not be discussed in detail. Suitably, the pharmaceutical compositions may be in the form of liquids and solutions suitable for intravenous injection in liquid dosage forms as appropriate and in unit dosage forms suitable for easy administration of fixed dosages. The dosage of the radiopharmaceutical depends upon many factors that are well known to those skilled in the art, for example, the type and pharmacodynamic characteristics of the radiopharmaceutical; age, weight and general health condition of the subject; nature and extent of symptoms; any concurrent therapeutic treatments; frequency of treatment and the effect desired.

In one aspect, the invention is directed to a method for diagnosing or treating cancer in a subject. In one embodiment, the cancer is selected from a cancer of the brain, lung, breast, pancreas, kidney, colon, rectum, ovary, prostate, head, neck, thyroid, bladder, bone, endometrium, testicular cancer, gastric cancer, or neuroblastoma. In one embodiment, the cancer is breast cancer. The method comprises administering an effective amount of a radiopharmaceutical to the subject and imaging cancer tissue using positron emission tomography. The radiopharmaceutical is capable of being retained within cancer tissue sufficient to emit positrons for detection by positron emission tomography.

In one aspect, the invention provides a method for monitoring cancer in a subject. The method comprises administering an effective amount of a radiopharmaceutical to a subject undergoing medical treatment for cancer, imaging cancer tissue using positron emission tomography, and comparing the quantity or distribution of the radiopharmaceutical present in the subject with a control quantity or distribution indicative of the effectiveness of the medical treatment.

Embodiments of the present invention are described in the following Examples, which are set forth to aid in the understanding of the invention, and should not be construed to limit in any way the scope of the invention as defined in the claims which follow thereafter.

EXAMPLE 1

Preparation of 6-Deoxy-6-Fluoro-D-Fructose

Reactions were carried out in flame-dried glassware under a positive argon atmosphere unless otherwise stated. Transfer of anhydrous solvents and reagents was accomplished with oven-dried syringes or cannulae. Solvents were distilled before use: methylene chloride ($CH_2Cl_2$) from calcium hydride, and pyridine from KOH. Thin layer chromatography was performed on glass plates precoated with 0.25 mm Kieselgel™ 60 $F_{254}$ (Merck). Flash chromatography columns were packed with 230-400 mesh silica gel (Silicycle). Optical rotations were measured at 22±2° C. Proton nuclear magnetic resonance spectra ($^1$H NMR) were recorded at 400 MHz or 500 MHz and coupling constants (J) are reported in Hertz (Hz). Standard notation was used to describe the multiplicity of signals observed in $^1$H NMR spectra: broad (br), multiplet (m), singlet (s), doublet (d), triplet (t), etc. Carbon nuclear magnetic resonance spectra ($^{13}$C NMR) were recorded at 100 MHz or 125 MHz and are reported (ppm) relative to the center line of the triplet from chloroform-d (77.00 ppm). Infrared (IR) spectra were measured with a Mattson Galaxy Series™ FT-IR 3000 spectrophotometer. Mass spectra were determined on a PerSeptive Biosystems Mariner™ high-resolution electrospray positive ion mode spectrometer.

EXAMPLE 2

Preparation of Methyl Fructofuranosides

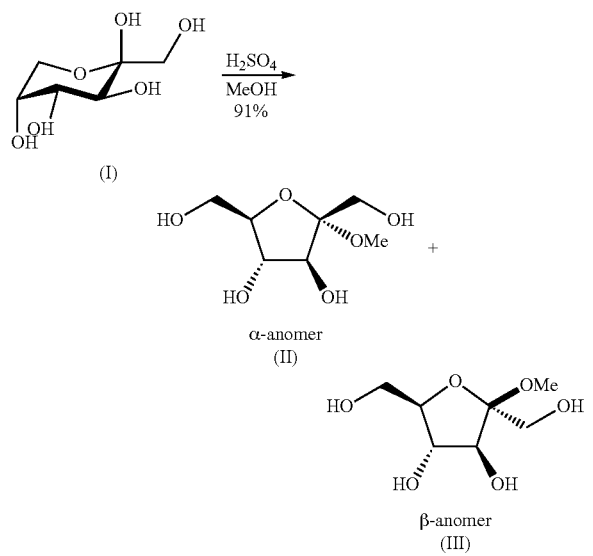

Fructose (180 g/mol, 6 g, 33.3 mmol) was dissolved in methanol (100 mL) at room temperature. Upon complete dissolution, $H_2SO_4$ (1.8 mL) was added at room temperature and the reaction left to stir for 50 min. The reaction was then quenched by the addition of $NH_4OH$ (aq.), which was added until the reaction mixture was neutralized. The white precipitate ($NH_4SO_4$) was removed by filtration and the solvent removed in vacuo to furnish a clear, colorless oil. The α/β-anomers were separated and purified using flash column chromatography (silica gel, 10% MeOH in $CH_2Cl_2$) and their structures confirmed by close agreement to previously reported spectral data (Duker et al., 1993). The α-anomer (2.82 g, 14.5 mmol, 44%) and β-anomer (2.95 g, 15.2 mmol, 46%) were carried through the subsequent steps separately.

EXAMPLE 3

Preparation of Methyl 6-O-(tert-butyldimethylsilyl)-α/β-D-fructofuranosides

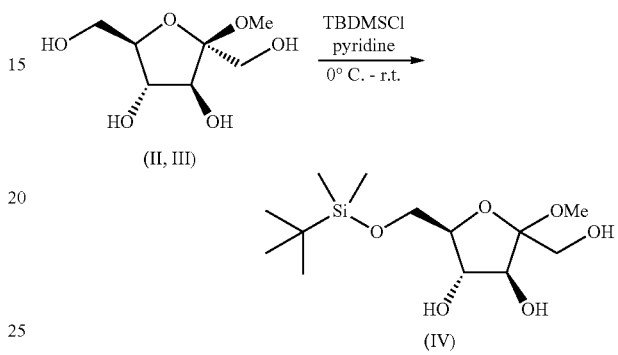

The methyl α/β-D-fructofuranoside (1.1 g, 5.6 mmol) was dissolved in freshly distilled pyridine (0.5 M). The reaction mixture was cooled to about 0° C. (ice/water bath) and TBDMSCl (7.3 mmol, 1.1 g) was added in a single portion. The reaction was left to stir overnight with gradual warming to room temperature. After overnight stirring, the reaction was quenched by the addition of water and dilution with $CH_2Cl_2$. The organic/aqueous layers were separated and the aqueous layer extracted with $CH_2Cl_2$ (2×15 mL). The combined organic layers were washed with 10% $H_2SO_4$ solution and water. The organic layer was dried ($MgSO_4$) and filtered before removing the solvent in vacuo. The 1,6-di-O-silylated product (0.071 g, 0.17 mmol, 3%) was isolated as a clear, colourless oil, while the desired 6-O-silylated product (1.0 g, 3.3 mmol, 58%) was obtained as a white solid after purification by flash column chromatography (silica gel, 5% MeOH in $CH_2Cl_2$).

(α): m.p. 68-70° C.; $R_f$ 0.34 ($CH_2Cl_2$/MeOH 49:1); $[α]_D$ +62.2 (c 0.6, MeOH); IR (thin film) 3453, 3322, 2952, 2929, 2858, 1461, 1253, 1150, 1072, 1009 cm$^{-1}$; $^1$H NMR (500 MHz, $CDCl_3$) δ 4.22 (d, J=11.0 Hz, 1H), 4.15 (br s, 1H), 4.05 (br d, J=11.5 Hz, 1H), 3.99 (d, J=11.0 Hz, 1H), 3.84 (d, J=6.5 Hz, 2H), 3.83 (m, 2H), 3.37 (s, 3H), 3.12 (d, J=11.5 Hz, 1H), 2.03 (t, J=7.0 Hz, 1H), 0.92 (s, 9H), 0.13 (s, 6H); $^{13}$C NMR (125 MHz, $CDCl_3$) δ 109.9, 86.6, 78.8, 78.2, 63.2, 58.2, 50.4, 48.6, 25.7, 18.3, −5.6 (2C); HRMS (ESI, [M+Na]$^+$) for $C_{13}H_{28}O_6SiNa$ calcd 331.1547, found: m/z 331.1545.

(β): m.p. 107-108° C.; $R_f$ 0.18 ($CH_2Cl_2$/MeOH 49:1); $[α]_D$ −21.8 (c 0.5, MeOH); IR (thin film) 3390, 2952, 2929, 2858, 1463, 1255, 1130, 1036, 837 cm$^{-1}$; $^1$H NMR (500 MHz, $CDCl_3$) δ 4.18 (br s, 1H), 4.14 (t, J=7.0 Hz, 1H), 3.85 (dt, J=7.0, 5.0 Hz, 1H), 3.75 (d, J=5.0 Hz, 2H), 3.69 (br s, 2H), 3.38 (br s, 1H), 3.35 (s, 3H), 3.29 (br s, 1H), 2.66 (br s, 1H), 0.91 (s, 9H), 0.09 (s, 6H); $^{13}$C NMR (125 MHz, $CDCl_3$) δ 103.2, 81.9, 79.0, 77.1, 64.1, 61.3, 49.2, 25.9, 18.4, −5.4 (2C); HRMS (ESI, [M+Na]$^+$) for $C_{13}H_{28}O_6SiNa$ calcd 331.1547, found: m/z 331.1546.

EXAMPLE 4

Preparation of Methyl 1,3,4-tri-O-acetyl-6-O-(tert-butyldimethylsilyl)-α/β-D-fructofuranosides

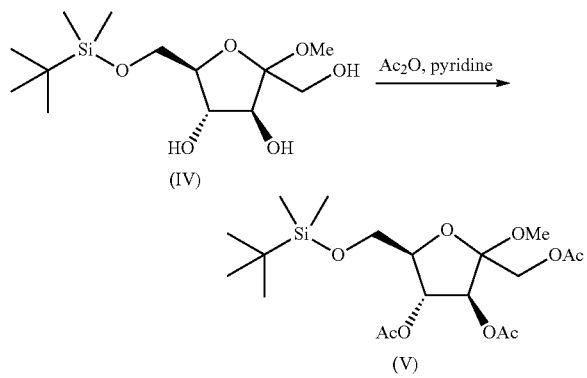

Methyl 6-O-(tert-butyldimethylsilyl)-α/β-D-fructofuranoside (0.94 g, 3.0 mmol) was dissolved in freshly distilled pyridine (0.25 M). The temperature of the reaction mixture was dropped to 0° C. (ice/water bath) and acetic anhydride (61.0 mmol, 5.8 mL) was added at low temperature via syringe. The reaction mixture was allowed to stir overnight with gradual warming to room temperature. The reaction was then quenched by the addition of water with subsequent stirring for 30 min. The reaction mixture was then diluted with $CH_2Cl_2$. The organic/aqueous layers were separated and the aqueous layer extracted with $CH_2Cl_2$ (2×10 mL). The combined organic layers were washed with 10% $H_2SO_4$ solution and water. The organic layer was then dried ($MgSO_4$) and filtered before removing the solvent in vacuo. Methyl 1,3,4-tri-O-acetyl-6-O-(tert-butyldimethylsilyl)-α/β-D-fructofuranoside (1.15 g, 2.6 mmol, 87%) was isolated as a pale yellow oil after purification by flash column chromatography (silica gel, 2% MeOH in $CH_2Cl_2$).

(α): $R_f$ 0.82 ($CH_2Cl_2$/MeOH 49:1); $[α]_D$ +75.6 (c 0.6, MeOH); IR (thin film) 2955, 2931, 2858, 1752, 1371, 1231, 1070, 838 $cm^{-1}$; $^1$H NMR (500 MHz, $CDCl_3$) δ 5.28 (d, J=2.0 Hz, 1H), 5.04 (dd, J=5.5, 2.0 Hz, 1H), 4.42 (d, J=12.0 Hz, 1H), 4.08 (d, J=12.0 Hz, 1H), 3.99 (dt, J=5.5, 4.5 Hz, 1H), 3.84 (d, J=4.5 Hz, 2H), 3.30 (s, 3H), 2.08 (s, 3H), 2.06 (s, 3H), 2.04 (s, 3H), 0.90 (s, 9H), 0.07 (s, 3H), 0.07 (s, 3H); $^{13}$C NMR (125 MHz, $CDCl_3$) δ 170.2, 170.0, 168.9, 106.6, 82.8, 80.5, 78.1, 62.4, 58.3, 48.5, 25.8, 20.8, 20.7, 20.6, 18.3, −5.3, −5.4; HRMS (ESI, [M+Na]$^+$) for $C_{19}H_{34}O_9SiNa$ calcd 457.1864, found: m/z 457.1864.

(β): $R_f$ 0.82 ($CH_2Cl_2$/MeOH 49:1); $[α]_D$ −8.0 (c 0.7, MeOH); IR (thin film) 2956, 2932, 2858, 1754, 1369, 1230, 1055, 839 $cm^{-1}$; $^1$H NMR (500 MHz, $CDCl_3$) δ 5.51 (t, J=7.0 Hz, 1H), 5.46 (d, J=7.0 Hz, 1H), 4.24 (d, J=12.0 Hz, 1H), 4.16 (d, J=11.5 Hz, 1H), 4.02 (q, J=5.5 Hz, 1H), 3.81 (dd, J=11.0, 5.0 Hz, 1H), 3.74 (dd, J=11.0, 5.5 Hz, 1H), 3.38 (s, 3H), 2.12 (s, 3H), 2.10 (s, 3H), 2.07 (s, 3H), 0.90 (s, 9H), 0.08 (s, 3H), 0.07 (s, 3H); $^{13}$C NMR (125 MHz, $CDCl_3$) δ 170.2, 170.1, 170.0, 102.7, 80.3, 77.1, 75.7, 63.5, 62.8, 49.8, 25.8, 20.8, 20.8, 20.7, 18.3, −5.5, −5.5; HRMS (ESI, [M+Na]$^+$) for $C_{19}H_{34}O_9SiNa$ calcd 457.1864, found: m/z 457.1864.

EXAMPLE 5

Preparation of Methyl 1,3,4-tri-O-acetyl-α/β-D-fructofuranosides

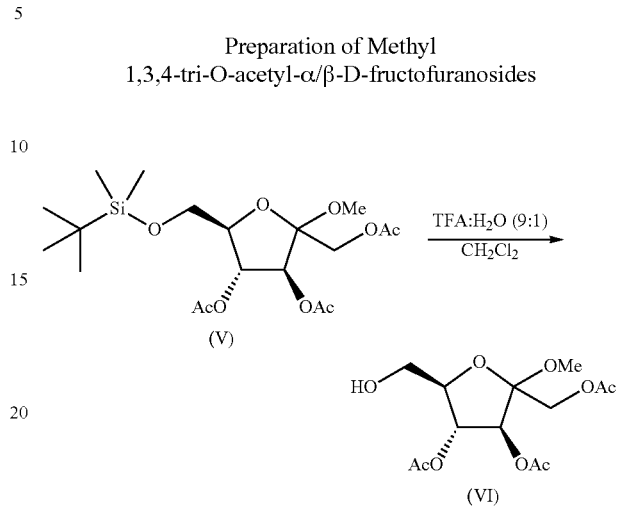

Methyl 1,3,4-tri-O-acetyl-6-O-(tert-butyldimethylsilyl)-α/β-D-fructofuranoside (0.98 g, 2.3 mmol) was dissolved in $CH_2Cl_2$ (25 mL). Water (1 mL) and trifluoroacetic acid (9 mL) were subsequently added via plastic syringe at room temperature. The reaction mixture was allowed to stir for 30 min. before being neutralized with the addition of 2N NaOH aq. solution. The organic/aqueous layers were separated and the aqueous layer extracted with $CH_2Cl_2$ (20 mL). The organic layer was then washed with saturated $NaHCO_3$ aq. and brine solution. The organic layer was dried ($MgSO_4$) and filtered before removing the solvent in vacuo. Methyl 1,3,4-tri-O-acetyl-α/β-D-fructofuranoside (0.48 g, 1.5 mmol, 65%) was obtained as a clear, colorless oil after purification by flash column chromatography (silica gel, 5% MeOH in $CH_2Cl_2$).

(α): $R_f$ 0.43 ($CH_2Cl_2$/MeOH 49:1); $[α]_D$ +95.8 (c 0.7, MeOH); IR (thin film) 3487, 2942, 1747, 1373, 1235, 1065, 892 $cm^{-1}$; $^1$H NMR (500 MHz, $CDCl_3$) δ 5.31 (d, J=2.0 Hz, 1H), 4.98 (dd, J=5.5, 2.5 Hz, 1H), 4.44 (d, J=12.5 Hz, 1H), 4.10 (d, J=12.0 Hz, 1H), 4.02 (q, J=4.0 Hz, 1H), 3.87 (ddd, J=12.0, 4.0, 4.0 Hz, 1H), 3.77 (ddd, J=12.5, 8.0, 4.5 Hz, 1H), 3.31 (s, 3H), 2.26 (dd, J=8.0, 5.0 Hz, 1H), 2.09 (s, 3H), 2.07 (s, 3H), 2.04 (s, 3H); $^{13}$C NMR (125 MHz, $CDCl_3$) δ 170.5, 170.1, 168.9, 106.5, 82.9, 79.8, 77.8, 61.9, 58.5, 48.6, 20.7, 20.7, 20.6; HRMS (ESI, [M+Na]$^+$) for $C_{13}H_{20}O_9Na$ calcd 343.0999, found: m/z 343.1000.

(β): $R_f$ 0.43 ($CH_2Cl_2$/MeOH 49:1); $[α]_D$ −13.7 (c 0.9, MeOH); IR (thin film) 3496, 2953, 1747, 1371, 1238, 1055, 905 $cm^{-1}$; $^1$H NMR (500 MHz, $CDCl_3$) δ 5.51 (d, J=7.5 Hz, 1H), 5.35 (t, J=6.0 Hz, 1H), 4.25 (d, J=12.0 Hz, 1H), 4.16 (d, J=12.0 Hz, 1H), 4.01 (q, J=6.0 Hz, 1H), 3.82 (ddd, J=11.5, 5.5, 5.5 Hz, 1H), 3.71 (ddd, J=12.0, 6.0, 6.0 Hz, 1H), 3.37 (s, 3H), 2.45 (t, J=6.5 Hz, 1H), 2.10 (s, 3H), 2.08 (s, 6H); $^{13}$C NMR (125 MHz, $CDCl_3$) δ 170.9, 170.1, 169.8, 102.4, 81.0, 77.2, 76.4, 76.1, 63.4, 62.3, 49.8, 20.8, 20.6, 20.6; HRMS (ESI, [M+Na]$^+$) for $C_{13}H_{20}O_9Na$ calcd 343.0999, found: m/z 343.1000. This data is in close agreement with the previously reported data (Tatibouet et al., 2000).

EXAMPLE 6

Methyl 1,3,4-tri-O-acetyl-6-deoxy-6-fluoro-αβ-D-fructofuranosides

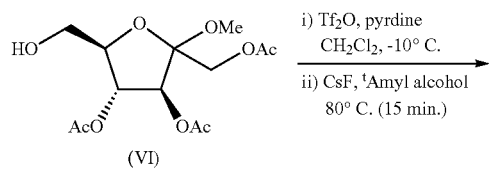

(VI)

i) Tf$_2$O, pyridine
CH$_2$Cl$_2$, -10° C.

ii) CsF, $^t$Amyl alcohol
80° C. (15 min.)

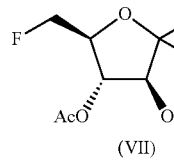

(VII)

Methyl 1,3,4-tri-O-acetyl-α/β-D-fructofuranoside (0.41 g, 1.3 mmol) was dissolved in freshly distilled CH$_2$Cl$_2$ (0.1 M, 13 mL). The temperature of the reaction was lowered to −10° C. (ice/acetone bath). Pyridine (1.9 mmol, 0.15 mL) and triflic anhydride (1.4 mmol, 0.24 mL) were subsequently added via syringe. The reaction mixture was allowed to stir at low temperature for 45 min. before being quenched with the addition of water. The organic/aqueous layers were separated and the aqueous layer extracted with CH$_2$Cl$_2$ (2×10 mL). The combined organic layers were washed with 10% H$_2$SO$_4$ solution and water. The organic layer was then dried (MgSO$_4$) and filtered before removing the solvent in vacuo. The 6-O-triflyl product was obtained as pale yellow oil.

The crude oil was directly dissolved in tert-amyl alcohol (0.33 M, 3.9 mL) and cesium fluoride (3.9 mmol, 0.58 g) was added in a single portion. The reaction was equipped with a reflux condenser and set to reflux at ~90° C. (oil bath). After 20 min, the reaction was cooled to room temperature, then water and CH$_2$Cl$_2$ were added. The organic/aqueous layers were separated and the aqueous layer extracted with CH$_2$Cl$_2$ (2×5 mL). The combined organic layers were washed with water (2×5 mL) and then dried (MgSO$_4$). After filtration, the solvent was removed in vacuo to provide an orange oil. Methyl 1,3,4-tri-O-acetyl-6-deoxy-6-fluoro-α/β-D-fructofuranoside (0.35 g, 1.1 mmol, 84%) was isolated as a clear, colourless oil after purification by flash column chromatography (silica gel, 5% MeOH in CH$_2$Cl$_2$).

(α): $R_f$ 0.55 (CH$_2$Cl$_2$/MeOH 49:1); $[\alpha]_D$ +74.7 (c 0.9, MeOH); IR (thin film) 2958, 1748, 1372, 1230, 1071, 892 cm$^{-1}$; $^1$H NMR (500 MHz, CDCl$_3$) δ 5.29 (br s, 1H), 4.93 (dd, J=5.5, 2.0 Hz, 1H), 4.65 (ddd, $^2J_{H-F}$=47.0 Hz, $J_{H-H}$=10.5, 2.5 Hz, 1H), 4.60 (ddd, $^2J_{H-F}$=47.0 Hz, $J_{H-H}$=10.5, 5.0 Hz, 1H), 4.44 (d, J=12.0 Hz, 1H), 4.14 (d, J=12.0 Hz, 1H), 4.10 (dddd, $^3J_{H-F}$=23.5 Hz, $J_{H-H}$=4.5, 4.5, 2.5 Hz, 1H), 3.31 (s, 3H), 2.10 (s, 3H), 2.07 (s, 3H), 2.03 (s, 3H); $^{13}$C NMR (125 MHz, CDCl$_3$) δ 170.2, 170.0, 168.9, 106.9, 81.8 (d, $^1J_{C-F}$=105.1 Hz), 81.1 (d, $^2J_{C-F}$=49.8 Hz), 79.6 (d, $^4J_{C-F}$=1.0 Hz), 77.2 (d, $^3J_{C-F}$=7.1 Hz), 58.0, 48.6, 20.6, 20.6, 20.6; HRMS (ESI, [M+Na]$^+$) for C$_{13}$H$_{19}$O$_8$FNa calcd 345.0956, found: m/z 345.0956.

(β): $R_f$ 0.55 (CH$_2$Cl$_2$/MeOH 49:1); $[\alpha]_D$ −28.1 (c 1.1, MeOH); IR (thin film) cm$^{-1}$; $^1$H NMR (300 MHz, CDCl$_3$) δ 5.52 (d, J=7.2 Hz, 1H), 5.40 (t, J=6.9 Hz, 1H), 4.63 (ddd, $^2J_{H-F}$=48.0 Hz, $J_{H-H}$=10.2, 3.0 Hz, 1H), 4.49 (ddd, $^2J_{H-F}$=47.4 Hz, $J_{H-H}$=10.5, 6.0 Hz, 1H), 4.26 (d, J=11.7 Hz, 1H), 4.17 (d, J=11.7 Hz, 1H), 4.16 (dddd, $^3J_{H-F}$=20.7 Hz, $J_{H-H}$=6.0, 6.0, 3.3 Hz, 1H), 3.38 (s, 3H), 2.11 (s, 3H), 2.09 (s, 3H), 2.09 (s, 3H); $^{13}$C NMR (125 MHz, CDCl$_3$) δ 170.3, 170.1, 169.9, 102.8, 82.5 (d, $^1J_{C-F}$=174.9 Hz), 78.9 (d, $^2J_{C-F}$=19.6 Hz), 76.3 (d, $^4J_{C-F}$=1.8 Hz), 74.7 (d, $^3J_{C-F}$=7.5 Hz), 62.1, 49.7, 20.7, 20.7, 20.7; HRMS (ESI, [M+Na]$^+$) for C$_{13}$H$_{19}$O$_8$FNa calcd 345.0956, found: m/z 345.0955.

EXAMPLE 7

Preparation of 6-Deoxy-6-fluoro-D-fructose

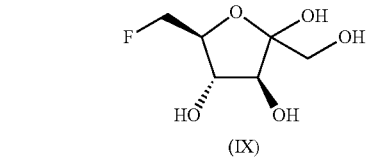

(VII)

i) NaOMe, MeOH ii) HCl (1 N)
1,4-dioxane

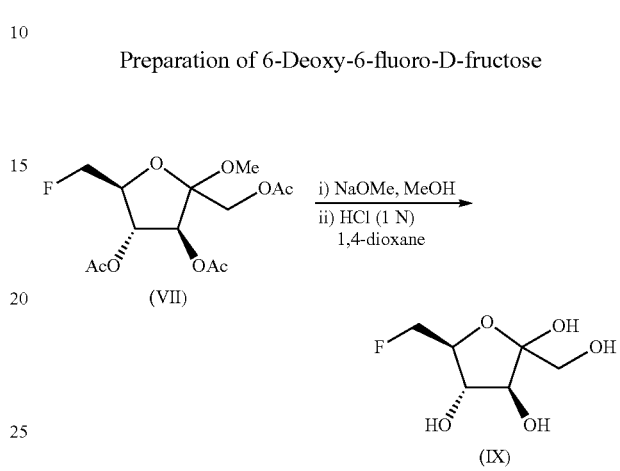

(IX)

Methyl 1,3,4-tri-O-acetyl-6-deoxy-6-fluoro-α/β-D-fructofuranoside (0.20 g, 0.62 mmol) was dissolved in anhydrous MeOH (6 mL). At room temperature, NaOMe in MeOH (1.5 M, 0.14 mL) was added to the reaction mixture via plastic syringe. The reaction was allowed to stir for 10 min. before the addition of 1N HCl to quench the reaction. Upon neutralization of the reaction mixture, the volatiles were removed in vacuo to provide a pale yellow residue.

The crude material from the previous reaction was directly dissolved in 1,4-dioxane (1.5 mL). 1N HCl aq. solution (1 mL) was then added and the reaction mixture allowed to stir at room temperature overnight. The reaction was then quenched by neutralization with the addition of 2N NaOH aq. solution. The solvent was removed in vacuo and the crude oil immediately purified by flash column chromatography (silica gel, 5-10% MeOH in CH$_2$Cl$_2$). 6-Deoxy-6-fluoro-D-fructose (6FDF) was obtained as a white solid (0.077 g, 0.42 mmol, 69%).

6FDF exists as an inseparable 1:4 mixture of α:β-anomers in the furanose conformation, as observed by $^1$H NMR in D$_2$O: m.p. 74-76° C.; $R_f$ 0.11 (CH$_2$Cl$_2$/MeOH 95:5); $[\alpha]_D$ −6.39 (c 1.8, MeOH); IR (thin film) 3339, 2954, 1649, 1454, 1048, 938 cm$^{-1}$; HRMS (ESI, [M+Na]$^+$) for C$_6$H$_{11}$O$_5$FNa calcd 205.0483, found: m/z 205.0484; Anal, Calcd for C$_6$H$_{11}$FO$_5$: C, 39.56; H, 6.09Found: C, 39.11; H, 6.07.

(α): Partial $^1$H NMR (500 MHz, D$_2$O) δ 4.69 (ddd, $^2J_{H-F}$=50.5 Hz, $J_{H-H}$=10.5, 2.5 Hz, 1H), 4.59 (ddd, $^2J_{H-F}$=47.5 Hz, $J_{H-H}$=11.0, 5.5 Hz, 1H), 3.67 (d, J=12.0 Hz, 1H), 3.64 (d, J=12.0 Hz, 1H); $^{13}$C NMR (125 MHz, CDCl$_3$) δ 105.6, 83.4 (d, $^1J_{C-F}$=167.4 Hz), 82.7, 80.6 (d, $^2J_{C-F}$=17.7 Hz), 76.1 (d, $^3J_{C-F}$=7.2 Hz), 63.6.

(β): $^1$H NMR (500 MHz, D$_2$O) δ 4.64 (ddd, $^2J_{H-F}$=47.5 Hz, $J_{H-H}$=11.0, 2.5 Hz, 1H), 4.56 (ddd, $^2J_{H-F}$=47.5 Hz, $J_{H-H}$=10.5, 5.0 Hz, 1H), 4.19 (t, J=8.5 Hz, 1H), 4.14 (d, J=8.5 Hz, 1H), 3.97 (dddd, $^3J_{H-F}$=24.0 Hz, $J_{H-H}$=8.0, 5.5, 2.5 Hz, 1H), 3.60 (d, J=12.0 Hz, 1H), 3.55 (d, J=12.0 Hz, 1H); $^{13}$C NMR (125 MHz, CDCl$_3$) δ 102.6, 83.9 (d, $^1J_{C-F}$=168.4 Hz), 79.7 (d, $^2J_{C-F}$=18.2 Hz), 75.9, 74.1 (d, $^3J_{C-F}$=7.5 Hz), 63.4.

EXAMPLE 8

Transport and accumulation of
6-deoxy-6-fluoro-D-fructose in breast cancer cells Methods Western Blots Isolated whole cell samples were lysed with Cellytic™ M (Sigma), and a Bradford protein quantification assay on total protein was used to determine the concentrations of the samples. The 25 µg samples were then run on a 10% separating gel, and then transferred to a nitrocellulose membrane. The protein was labelled using specific rabbit primary polyclonal antibodies of the GLUT isoform being examined at each of their respective concentrations. After the primary antibody was applied overnight, it was labelled with ECL™ Antirabbit IgG Horseradish peroxidase linked whole antibody and then was visualized using the ECL™ Western Blot detection reagents (Amersham Biosciences).

Cell Culture and Fluxes

Both MCF-7 and MDA-MB-231 cells (Gifts from Dr. David Murray, Cross Cancer Institute, Edmonton, Canada) were grown in a 37° C., 5% $CO_2$ incubator, in Gibco® DMEM-F12 supplemented with 15 mM HEPES, L-glutamine, 10% fetal bovine serum and 1% penicillin/streptomycin with media renewal every 2 to 3 days. For cell flux studies, cells were grown to confluence in 12-well plates with media renewal every two days. Two hours before performing the flux experiment, the media was removed, and the cells washed twice with phosphate buffered saline solution (PBS). Glucose-free Krebs-Ringer solution was added to the wells (120 mM NaCl, 25 mM $NaHCO_3$, 4 mM KCl, 1.2 mM $KH_2PO_4$, 2.5 mM $MgSO_4$, 70 uM $CaCl_2$, pH 7.4) to deprive the cells of nutrients and to set up a zero-trans experiment. After two hours, cells were removed from the incubator, and the respective experiments were performed. Radioactive "Hot" flux solutions were made up using the Krebs-Ringer solution previously mentioned and radiolabelled [$^{14}$C]-D-glucose (Amersham), [$^{14}$C]-D-fructose (Moravek Biochemicals), or [$^{14}$C]6FDF (proprietary) at a specific activity of approximately 1 µCi/ml. For determining background levels of radioactivity, a sodium reduced Krebs solution was made (70 mM NaCl, 25 mM $NaHCO_3$, 4 mM KCl, 1.2 mM $KH_2PO_4$, 2.5 mM $MgSO_4$, 70 µM $CaCl_2$, pH 7.4) with the addition of either 100 mM D-glucose or 100 mM D-fructose to outcompete the binding sites of the specific GLUT transporters under examination. After applying the test flux solution, incubations lasted for 25 minutes, where the cells were then rinsed twice with ice-cold Krebs-Ringer to stop the transport, and then lysed using 500 µl 5% trichloracetic acid and left to sit on a shaker bed overnight. Three 150 µl samples from each well were placed into scintillation counter vials, and 4 ml of ScintiSafe™ liquid scintillation fluid (Fisher) was added. The vials were then placed in a Beckman™ LS 6500 multi-purpose liquid scintillation counter to be quantified. All counts were then normalized to standards and corrected for background accumulation of isotope.

Immunocytochemistry

Cells were grown on 25 mm glass coverslips in 6-well plates until they were at the desired confluence. The cell culture media was removed, and the cells were rinsed twice with PBS. 50% methanol/PBS solution was added into the wells, and left on a shaker at a low speed for five minutes. The PBS/Methanol solution was aspirated, and 100% methanol was added to each well before putting the cells into a –20° C. freezer to be stored until needed. After removing the cells from the freezer for immunofluorescence, the methanol was aspirated, and PBS was added and left to rinse the cells on the shaker for five minutes. The PBS was then aspirated, and a 5% skim milk solution was left on the cells to block for 1 hour. Primary antibody solutions were then prepared in the 5% skim milk solution at concentrations appropriate for each individual GLUT isoform (GLUT1, 2—Chemicon, GLUT5—Biogenesis, GLUT7—Chemicon, GLUT9—Gift from Dr. Kelle Molle, GLUT12—Gift from Dr. Sue Rogers). The antibody solutions were then placed on the coverslips and let sit at room temperature for one hour. The coverslips were rinsed in a 0.01% PBS-Tween solution. The secondary antibody (anti-rabbit Alexaflour 488-Invitrogen) was allowed to bind to the primary antibody for another hour and then the coverslips with the cells were washed in PBS. The coverslips were then mounted on slides using ProLong™ Gold antifade reagent with DAPI (Invitrogen) before leaving to dry for 30 minutes and then being placed in darkness in a 4° C. refrigerator.

Kinetic Analysis

All uptake values were corrected for their respective adhering extracellular substrate, and $K_i$ values were determined using non-linear regression in GraphPad Prism™ 5 (GraphPad Software, Inc., La Jolla, Calif.). ANOVA analysis was also performed in GraphPad Prism™ 5.

Figure 3:
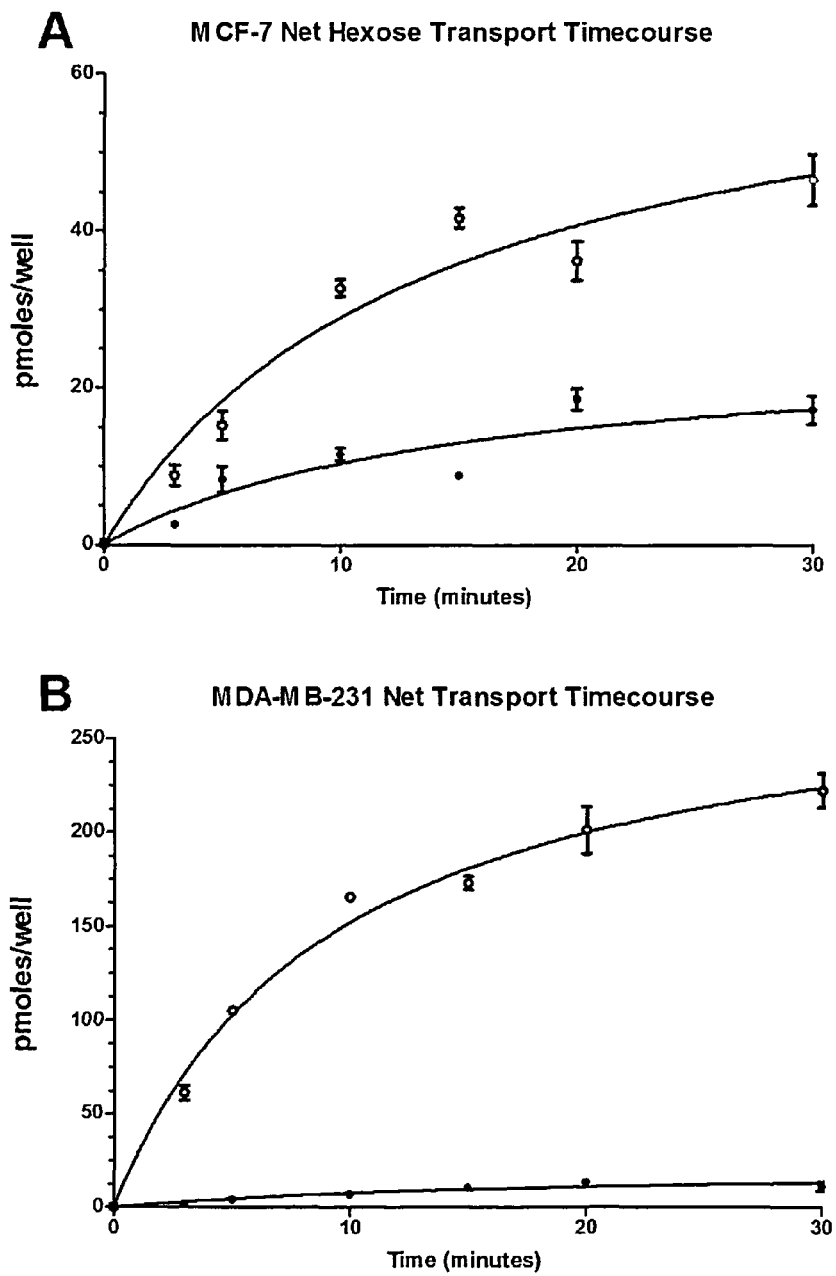
FIG. 3 shows the results of hexose flux assays with both fructose (•) and glucose (°) in both MCF-7 (A) and MDA-MB-231 (B) which show clear uptake after being corrected for non-carrier mediated uptake of hexose. MDA-MB-231 has significantly higher uptake of glucose compared to that of MCF-7, while fructose uptake in both cell lines is similar. Each data point represents n=3 and the error bars are the standard errors.

As shown in FIG. 3, hexose uptake and the pattern of expression of specific GLUT5 in two human breast cancer cell lines (MCF-7 and MDA-MB-231) were initially characterized. A cell culture transport model was utilized with these particular cell lines based on their use in recent investigations of fructose transport in breast tumours and their representation of early and late stage breast cancer, respectively (Chan et al., 2004; Levi et al., 2007). Initially, experiments were conducted to ascertain the ability of both MDA-MB-231 and MCF-7 to transport glucose and fructose. A 30 minute time course was performed with [$^{14}$C]-D-glucose and [$^{14}$C]-D-fructose and, after correcting the data for residual extracellular levels of hexose, uptake of both substrates was observed with what appears to be the start of a plateau at around 30 minutes. MDA-MB-231 cells showed a much higher level of glucose uptake than MCF-7 cells, and fructose transport was comparable between the two cell lines. The large disparity in glucose transport between the two cell lines is most likely indicative of differential levels of GLUT1 in the membrane (Laudanski et al., 2003).

Figure 4:
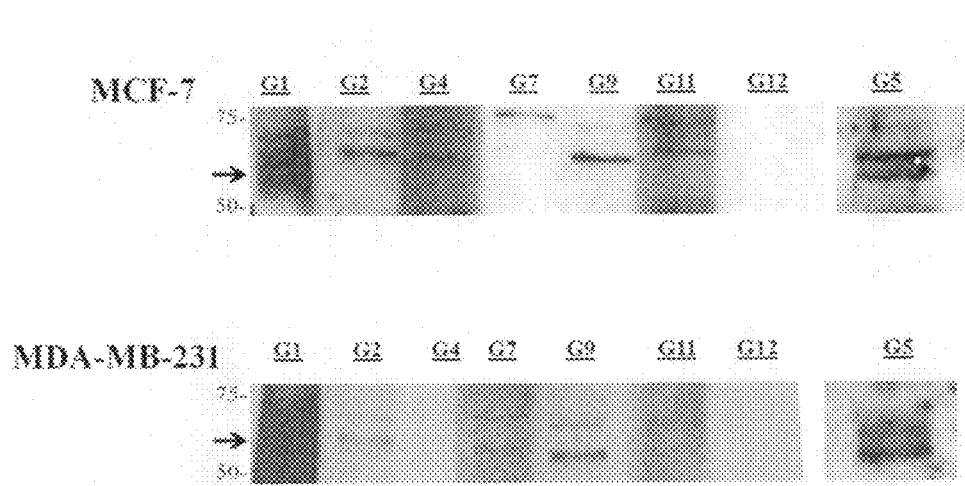
FIG. 4 shows Western immunoblots of MCF-7 (A) and MDA-MB-231 (B) using 25 μg of whole cell protein. The protein ladder indicates the location of 75 KDa and 50 KDa sized bands and the arrow refers to the approximate location of each of the GLUT isoforms to appear if detected. The doublet represents both glycosylated and unglycosylated copies of the isoform.
Figure 5:
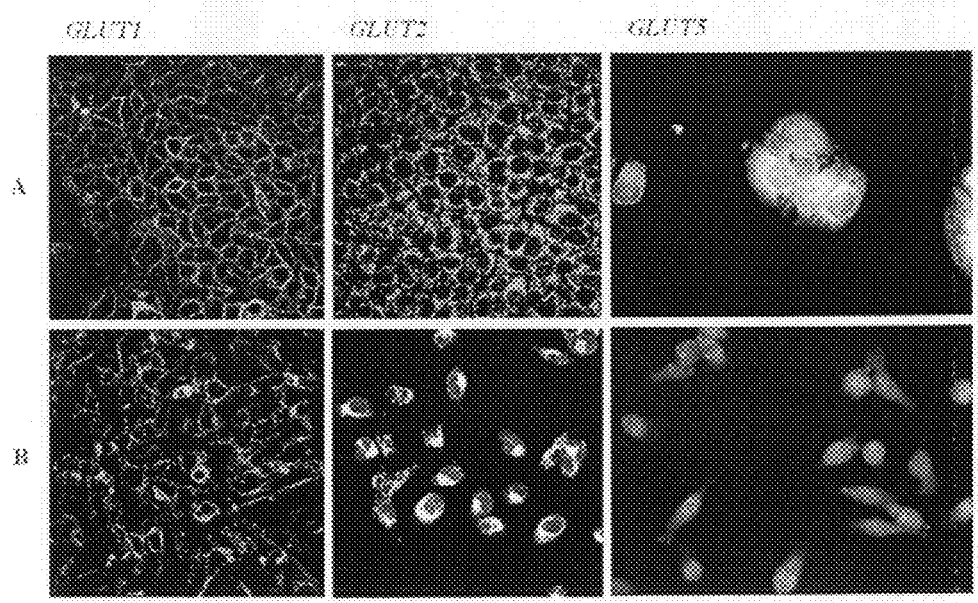
FIG. 5 shows confocal images of both MCF-7 (A) and MDA-MB-231 (B) labelled using anti-GLUT1, GLUT2, and GLUT5 antibodies.

MCF-7 and MDA-MB-231 cells are known to express several GLUT isoforms. Several techniques were used to identify which GLUTs contribute to glucose and fructose transport. Western immunoblots utilizing a wide range of anti-GLUT antibodies were conducted (FIG. 3), allowing visualization of isoforms which may contribute to total transport in the cell lines, and to confirm previous expression data (Zamora-Leon et al., 1996; Chan et al., 2004; and Laudanski et al., 2003). Immunocytochemistry provided information regarding the localization of the GLUT proteins detected in the Western blots and isoform contributions to uptake due to their presence in the membrane (FIG. 4). Class I GLUT inhibitor cytochalasin B[24] (FIGS. 6 and 10) inhibits fructose transport mediated by GLUT2, thus by subtraction, provides direct insight into the contribution of GLUT5 to the total fructose flux. While both the Western blots and immunocytochemistry clarified some characteristics of hexose transport in the cells, functional data presents a much more definitive picture.

Figure 6:
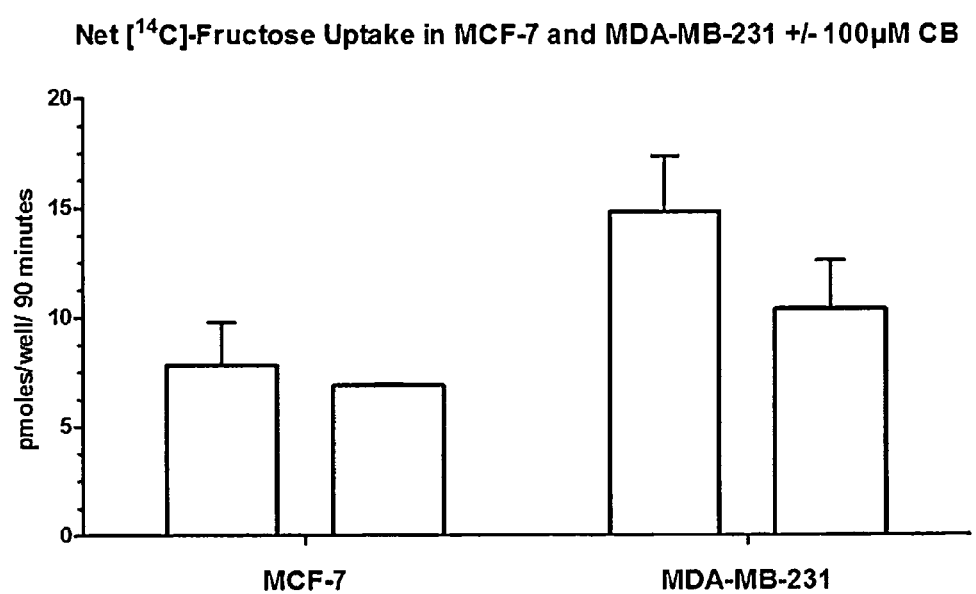
FIG. 6 shows 90 minute flux using $[^{14}C]$D-fructose performed on both cell lines with and without treatment with 100 μM of the Class I GLUT inhibitor cytochalasin B (+CB represented by the shaded bars). Inhibition of the Class I GLUT isoform GLUT2 is apparent in both lines, although a much larger inhibition is shown in MDA-MB-231. All values are corrected for non-mediated hexose uptake and each data point represents n=3.

Western blots utilizing 25 µg of total protein obtained from both MCF-7 and MDA-MB-231 (FIG. 4) indicate that both cell lines express similar levels of GLUT5, while MCF-7 had higher relative expression of the glucose/fructose-transporting isoform GLUT2. Functional data indicates that MDA-MB-231 has much higher membrane expression of GLUT2 (FIG. 6). Immunocytochemistry shows clear cytosolic and membrane expression of both fructose transporting isoforms. The major glucose-transporting isoform, GLUT1, was much more highly expressed within MDA-MB-231 compared to MCF-7. Low levels of GLUT9 are also present in both cell lines and appear to be localized in the perinuclear region (data not shown). The localization and recent recognition of GLUT9 as a mediator of urate transport (Caulfield et al., 2008) suggests that it would have very minimal influence on the total hexose flux across the membrane. Despite previous reports (Macheda et al., 2005), neither the Western blots nor immunocytochemistry indicated the presence of GLUT12 in MCF-7, while lack of expression in MDA-MB-231 is consistent (immunocytochemistry data not shown). Both functional and Western blot data suggest that the MDA-MB-231 cell line displays more GLUT1 in the membrane compared to MCF-7 cells and consequently higher glucose flux observed in MDA-MB-231 cells (FIG. 4).

Figure 7:
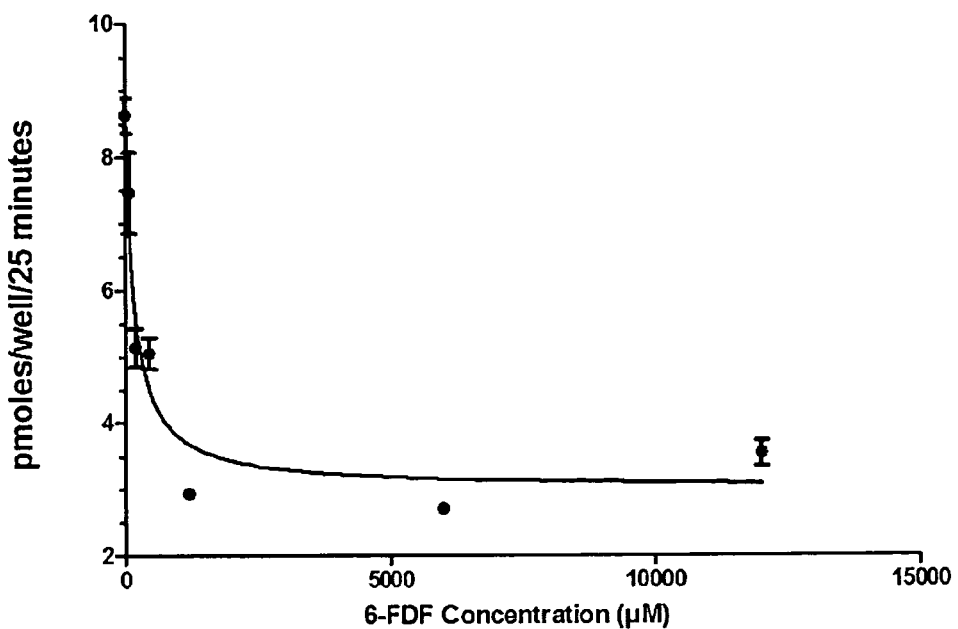
FIG. 7 shows the results of 6-deoxy-6-fluoro-D-fructose inhibition studies of [$^{14}$C]-D-glucose transport after a 25 minute incubation in both MCF-7 (A) and MDA-MB-231 (B) using increasing concentrations of 6-deoxy-6-fluoro-D-fructose. Glucose transport was inhibited by 6-deoxy-6-fluoro-D-fructose with a $K_i$ of approximately 916±230 µM in MCF-7 (A) and a $K_i$ of 6212±2860 µM in MDA-MB-231 (B). Each data point represents n=3 and the error bars are the standard errors.
Figure 7:
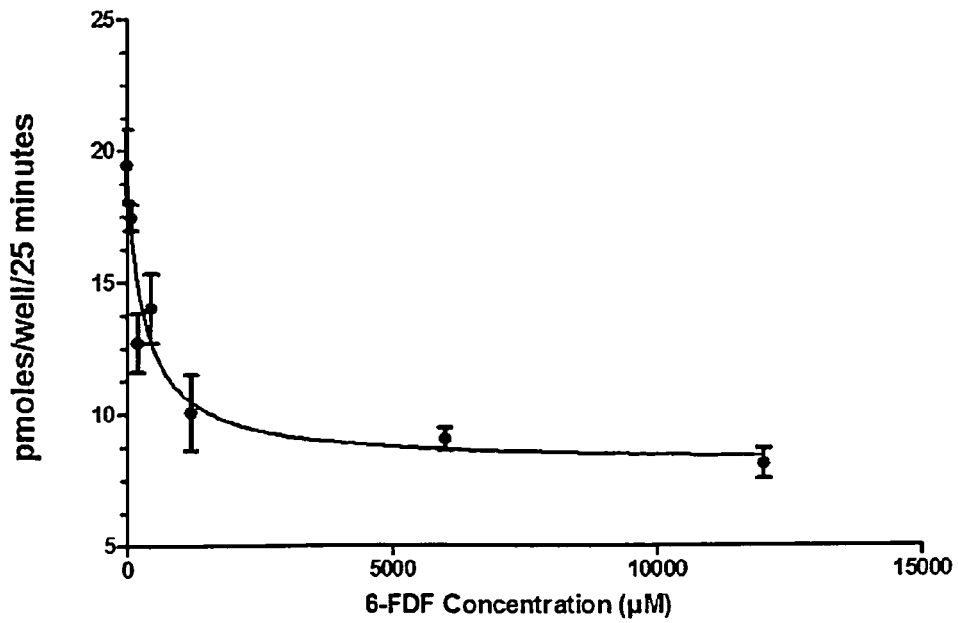

Localization analysis with immunocytochemistry showed that both GLUT2 and GLUT5 are present in the membrane and in the cytoplasm of the two cell lines (FIG. 6); however, functional data suggests that the quantities of each isoform in the membranes vary (FIG. 7). Data obtained utilizing $[^{14}C]$-D-fructose and treatment with 100 µM CB has shown that GLUT2 plays a minor part in the total fructose flux across the membrane of MCF-7 cells (about 12%), while in MDA-MB-231 cells approximately 30% of the total fructose flux is mediated by GLUT2. These results provide evidence that GLUT5 mediates the largest component of fructose transport in both cell lines. Recognition of the minor influence of GLUT2 on the total fructose flux, and knowledge of GLUT5 in human breast cancer prompted selection of MCF-7 cells as a model system for further investigation into the transportability of 6-deoxy-6-fluoro-D-fructose.

Figure 8:
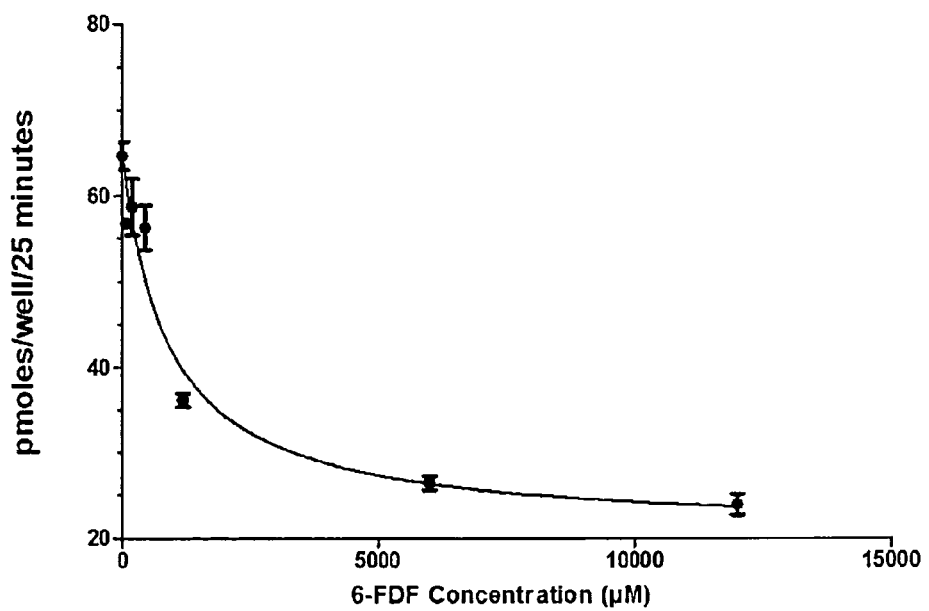
FIG. 8 shows the results of 6-deoxy-6-fluoro-D-fructose inhibition studies of [$^{14}$C]-D-fructose transport after a 25 minute incubation in both MCF-7 (A) and MDA-MB-231 (B) using increasing concentrations of 6-deoxy-6-fluoro-D-fructose. Fructose transport was inhibited by increasing concentrations of 6-deoxy-6-fluoro-D-fructose, and the $K_i$ obtained for MCF-7 (A) was 154±54 µM and MDA-MB-231 (B) had a $K_i$ of 330±153 µM. Each data point represents n=3 and the error bars are the standard errors.
Figure 8:
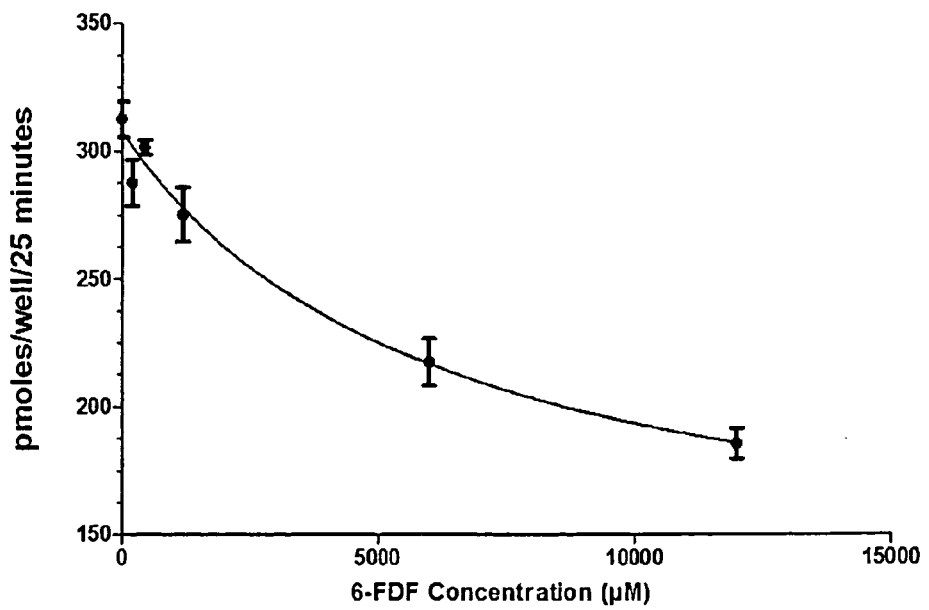

Substrate competition and inhibition of fructose and glucose transport by 6-deoxy-6-fluoro-D-fructose were then examined. In hexose transport inhibition studies of MCF-7 and MDA-MB-231 cells, close dependent inhibition of $[^{14}C]$-D-fructose and $[^{14}C]$-D-glucose transport was observed by increasing the concentrations of 6-deoxy-6-fluoro-D-fructose in the incubation media. The influence of GLUT2 on the total flux was evidence that glucose transport can be inhibited by 6-deoxy-6-fluoro-D-fructose with a $K_i$ of approximately 0.916±0.230 mM in MCF-7 (FIG. 7A) and a $K_i$ of 6.21±2.86 mM in MDA-MB-231 (FIG. 7B). More importantly, fructose transport was also clearly inhibited by increasing concentrations of 6-deoxy-6-fluoro-D-fructose, and the $K_i$ obtained for MCF-7 was 154±54 µM (FIG. 8A) and MDA-MB-231 had a $K_i$ of 330±153 µM (FIG. 8B).

Inhibition of fructose transport by 6-deoxy-6-fluoro-D-fructose indicates that the fluorinated fructose analogue can bind to both GLUT2 and GLUT5 with high affinity in both cell lines. Glucose transport inhibition by 6-deoxy-6-fluoro-D-fructose is also a strong indicator that 6-deoxy-6-fluoro-D-fructose binds to GLUT2. While the inhibition of both glucose and fructose transport is evidence for binding, confirmation of transport into the cells demonstrates that 6-deoxy-6-fluoro-D-fructose is moved across the membrane. To perform uptake experiments, $[^{14}C]$-labelled 6-deoxy-6-fluoro-D-fructose was synthesized using the described process (FIG. 1) and $[^{14}C]$-fructose as the starting material. The synthesis of $[^{14}C]$-6-deoxy-6-fluoro-D-fructose (SA~1 µCi/ml) was accomplished with a 13% overall yield. Only three purification steps were performed to limit unnecessary exposure to the radiolabelled compound.

Figure 9:
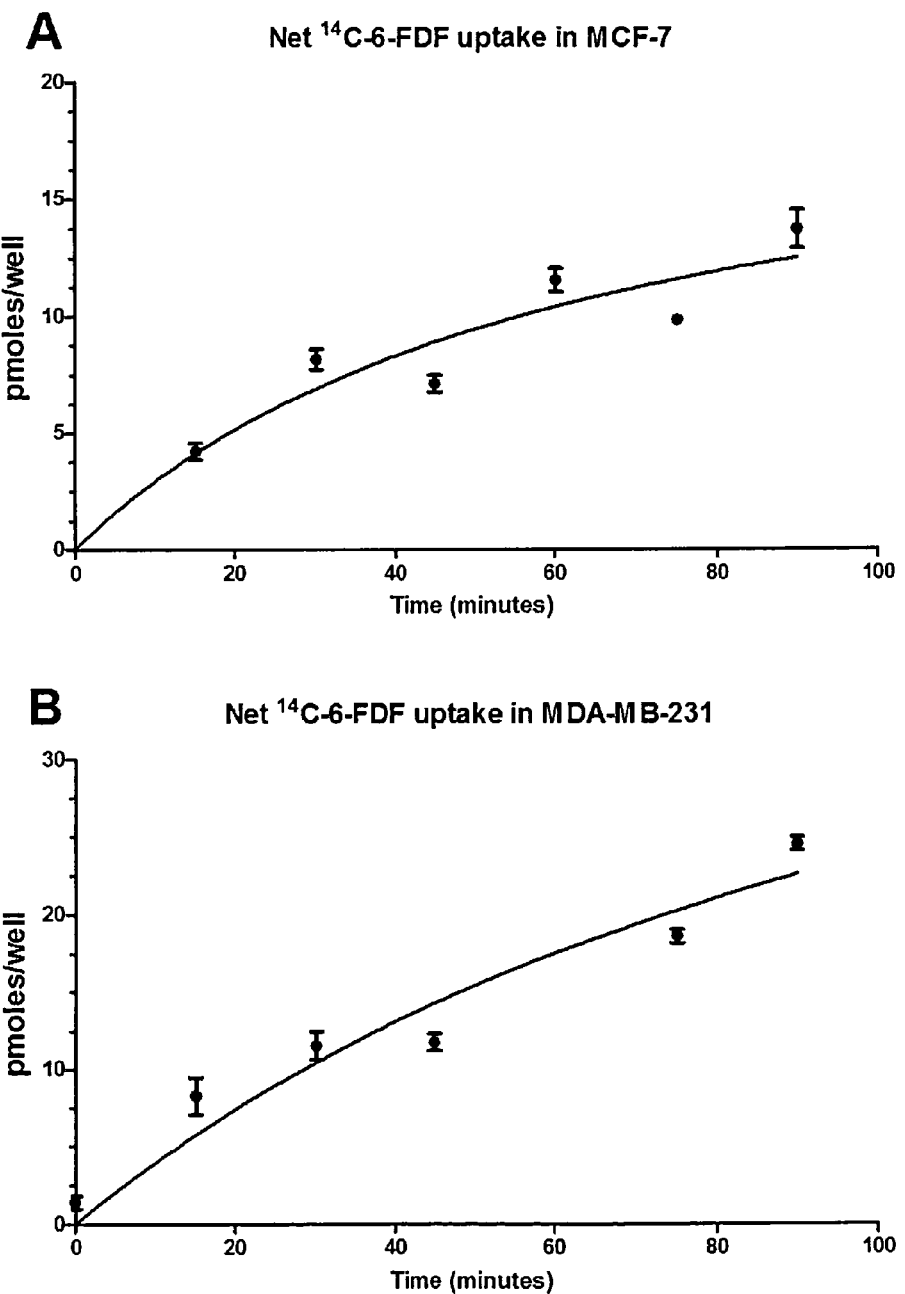
FIG. 9 shows [$^{14}$C]-6-deoxy-6-fluoro-D-fructose uptake time courses in both MCF-7 (A) and MDA-MB-231 (B) corrected for non-mediated hexose uptake. Near linear uptake is observed in both cell types after a 90 minute incubation and each data point represents n=3.
Figure 10:
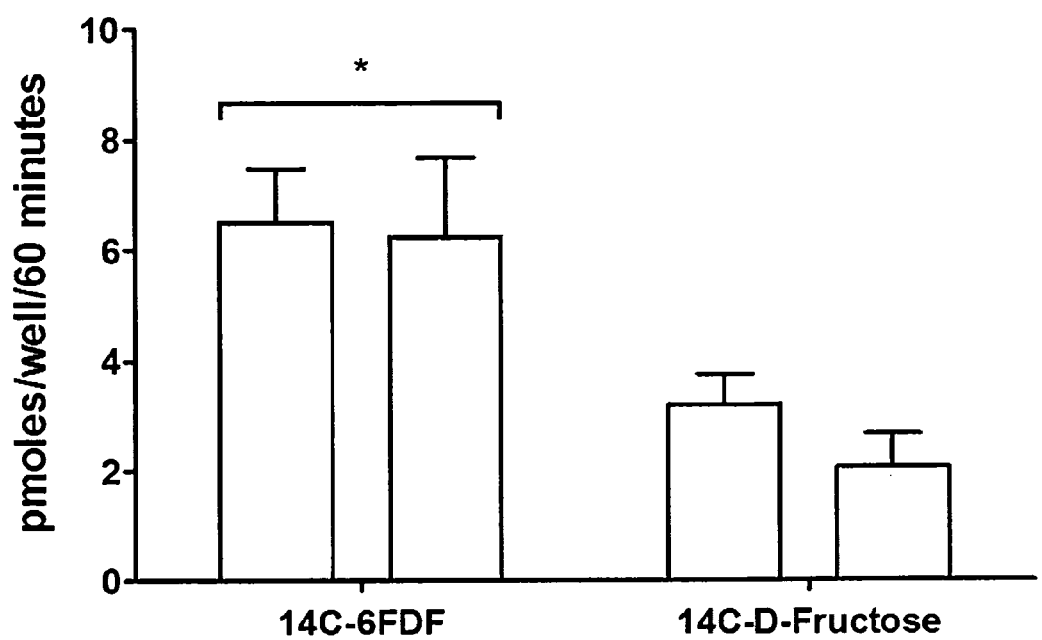
FIG. 10 shows inhibition by 100 µM cytochalasin B (+CB is represented by the shaded bars) of [$^{14}$C]-D-fructose and [$^{14}$C]-6-deoxy-6-fluoro-D-fructose uptake into MCF-7 cells. Incubations lasted 60 minutes and uptakes were corrected for non-mediated fluxes. 2-way ANOVA determined high statistical significance between 6-deoxy-6-fluoro-D-fructose and fructose transport groups (p=0.0028). Error bars represent the SEM.

A 90 minute time course experiment was performed for each cell line, using $[^{14}C]$-6-deoxy-6-fluoro-D-fructose and uptake was near linear over the entire time period (FIG. 9). Levi et al, (2007) report that neither MCF-7 nor MDA-MB-231 cells express fructokinase, suggesting that the potential for phosphorylation of a 6-fluorinated fructose compound would be limited; however, it may be that there are other interactions within the cell that prevent the efflux of 6-deoxy-6-fluoro-D-fructose from the cell. A comparison between $[^{14}C]$-6-deoxy-6-fluoro-D-fructose and $[^{14}C]$-D-fructose uptake in the GLUT5 model cell line (MCF-7) was performed (FIG. 9). After a one hour incubation, 2-way ANOVA analysis revealed a very significant (p=0.0028), almost two-fold increase, in uptake of $[^{14}C]$-6-deoxy-6-fluoro-D-fructose compared to $[^{14}C]$-D-fructose (FIG. 10). In addition, it was found that inhibition of GLUT2 using CB afforded no significant transport difference in either fructose or 6-deoxy-6-fluoro-D-fructose transport. This result confirms the previous observation that GLUT5 is the major contributor to fructose movement across the plasma membrane, while also strongly implicating GLUT5 in the successful transport of 6-deoxy-6-fluoro-D-fructose into MCF-7 cells. Such results demonstrate the ability of 6-deoxy-6-fluoro-D-fructose to inhibit fructose transport mediated by GLUT2 and GLUT5 with a very low $K_i$ and accumulation of $[^{14}C]$-6-deoxy-6-fluoro-D-fructose in both MCF-7 and MDA-MB-231 cells.

As will be apparent to those skilled in the art, various modifications, adaptations and variations of the foregoing specific disclosure can be made without departing from the scope of the invention claimed herein.

References

The following references are incorporated herein by reference (where permitted) as if reproduced in their entirety. All references are indicative of the level of skill of those skilled in the art to which this invention pertains.

Alavi, A. and Zhuang, H. (2001) Finding infection—help from PET. Lancet 358(9291):1386.

Bols, M. and Szarek, W. A. (1992) Synthesis of 3-deoxy-3-fluoro-D-fructose. J. Chem. Soc., Chem. Commun. Issue 5: 445-446.

Buck, A., Schirrmeister, H., Kuhn, T., Shen, C., Kalker, T., Kotzerke, J., Dankerl, A., Glatting, G., Reske, S, and Mattfeldt, T. (2002) FDG uptake in breast cancer: correlation with biological and clinical prognostic parameters. Eur J. Nucl. Med. Mol. Imaging. 29(10):1317-1323.

Buerkle A, W. W. (2008) Imaging of tumor glucose utilization with positron emission tomography. Cancer Metastasis Rev. 27(4):545-554.

Caulfield, M. J., Munroe, P. B., O'Neill, D., Witkowska, K., Charchar, F. J., Doblado, M., Evans, S., Eyheramendy, S., Onipinla, A., Howard, P., Shaw-Hawkins, S., Dobson, R. J., Wallace, C., Newhouse, S. J., Brown, M., Connell, J. M., Dominiczak, A., Farrall, M., Lathrop, G. M., Samani, N. J., Kumari, M., Marmot, M., Brunner, E., Chambers, J., Elliott, P., Kooner, J., Laan, M., Org, E., Veldre, G., Viigimaa, M., Cappuccio, F. P., Ji, C., Iacone, R., Strazzullo, P., Moley, K. H. and Cheeseman, C. (2008) SLC2A9 is a high-capacity urate transporter in humans, PLoS Med. 5(10):e197.

Chan, K. K., Chan, J. Y., Chung, K. K. and Fung, K. P. (2004) Inhibition of cell proliferation in human breast tumor cells by antisense oligonucleotides against facilitative glucose transporter 5. J. Cell. Biochem. 93:1134-1142.

Cheeseman, C. I., Grant, T. N., Trayner, B. and West, F. G. (2008) Synthesis of fluorinated fructose analogues for use with PET. Abstract: CSC 2008, 91$^{st}$ Canadian Chemistry Conference and Exhibition, May 24-28, 2008, Edmonton, Canada, published online May 18, 2008.

Crippa, F., Agresti, R., Seregni, E., Greco, M., Pascali, C., Bogni, A., Chiesa, C., De Sanctis, V., Delledonne, V., Salvadori, B., Leutner, M. and Bombardieri, E. (1998) Prospective evaluation of fluorine-18-FDG PET in presurgical staging of the axilla in breast cancer. *J Nucl. Med* 39(1):4-8.

Duker, J. M. and Serianni, A. S. (1993) (13C)-substituted sucrose: 13C-1H and 13C-13C spin coupling constants to assess furanose ring and glycosidic bond conformations in aqueous solution. Carbohydr. Res. 249(2):281-303.

Durrwachter, J. R., Drueckhammer, D. G., Nozaki, K., Sweers, H. M. and Wong, C. H. (1986) Enzymic aldol condensation/isomerization as a route to unusual sugar derivatives. J. Amer. Chem. Soc. 108(24):7812-7818.

Eubank, W. B.; Mankoff, D. A. (2005) Evolving role of positron emission tomography in breast cancer imaging. Semin. Nucl. Med. 35(2):84-99.

Fu, Y., Maianu, L., Melbert, B. R. and Garvey, W. T. (2004) Facilitative glucose transporter gene expression in human lymphocytes, monocytes, and macrophages: a role for GLUT isoforms 1, 3, and 5 in the immune response and foam cell formation. Blood Cells Mol. Dis. 32(2):182-190.

Godoy, A., Ulloa, V., Rodriguez, F., Reinicke, K., Yanez, A. J., Garcia Mde, L., Medina, R. A., Carrasco, M., Barberis, S., Castro, T., Martinez, F., Koch, X., Vera, J. C., Poblete, M. T., Figueroa, C. D., Peruzzo, B., Perez, F. and Nualart, F. (2006) Differential subcellular distribution of glucose transporters GLUT1-6 and GLUT9 in human cancer: ultrastructural localization of GLUT1 and GLUT5 in breast tumor tissues. J. Cell. Physiol. 207(3):614-627.

Hamberg, L. M., Hunter, G. J., Alpert, N. M., Choi, N. C., Babich, J. W. and Fischman, A. J. (1994) The dose uptake ratio as an index of glucose metabolism: useful parameter or oversimplification? J. Nucl. Med. 35(8):1308-1312.

Haradahita, T., Tanaka, A., Maeda, M., Kanazawa, Y., Ichiya, Y. I. and Masuda, K. (1995) Radiosynthesis, rodent biodistribution, and metabolism of 1-deoxy-1-[18F]fluoro-D-fructose. Nuclear Medicine and Biology 22(6):719-725.

Heaney, A. P., Hui, H. and Waxman, A. Use of fructose-based compounds for the diagnosis of cancer. International Publication No. WO 2007/025282 A2, published Mar. 1, 2007.

Kim, D. W., Ahn, D. S., Oh, Y. H., Lee, S., Kil, H. S., Oh, S. J., Lee, S. J., Kim, J. S., Ryu, J. S., Moon, D. H. and Chi, D. Y. (2006) A new class of SN2 reactions catalyzed by protic solvents: Facile fluorination for isotopic labeling of diagnostic molecules, J. Am, Chem. Soc. 128:16394-16397.

Kubota, R., Kubota, K., Yamada, S., Tada, M., Ido, T. and Tamahashi, N. J. (1994) Microautoradiographic study for the differentiation of intratumoral macrophages, granulation tissues and cancer cells by the dynamics of fluorine-18-fluorodeoxyglucose uptake. Nucl. Med. 35(1):104-112.

Kumar, R.; Alavi, A. (2004) Fluorodeoxyglucose-PET in the management of breast cancer. Radiol. Clin. North. Am. 42(6):1113-22.

Laudanski, P., Swiatecka, J., Kovalchuk, O. and Wolczynski, S. (2003) Expression of GLUT1 gene in breast cancer cell lines MCF-7 and MDA-MB-231. Ginekol Pol. 74:782-785.

Levi, J., Cheng, Z., Gheysens, O., Patel, M., Chan, C. T., Wang, Y., Namavari, M. and Gambhir, S. S. (2007) Fluorescent fructose derivatives for imaging breast cancer cells. Bioconjug. Chem. 18(3):628-634.

Macheda, M. L., Rogers, S, and Best, J. D. (2005) Molecular and cellular regulation of glucose transporter (GLUT) proteins in cancer. J. Cell. Physiol. 202:654-662.

What is claimed is:

1. A method of preparing the radiopharmaceutical of formula:

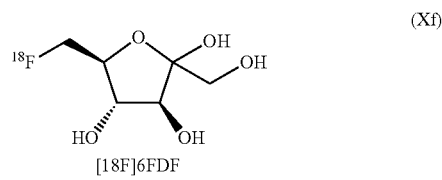 [SMILES: OCC1(O)O[C@H](C[18F])[C@@H](O)[C@@H]1O]

comprising reacting the compound of formula (X)

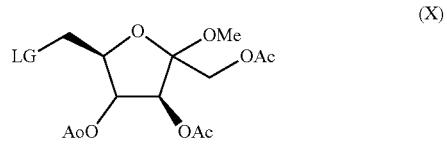

with a radioactive fluorinated complex to displace the leaving group to yield the radiopharmaceutical of formula (XI), wherein LG represents a leaving group, and wherein the leaving group is a trifluoromethanesulfonate (triflate), chloride, bromide, iodide, 4-nitrophenylsulfonate (nosylate), 4-methylphenylsulfonate (tosylate), or phenylsulfonate.

2. The method of claim 1, wherein the compound of formula (X) is reacted with [$^{18}$F]FK-K$_{222}$ activated complex in acetonitrile at 85° C., followed by addition of hydrochloric acid at 110° C.

3. A method for imaging cancer in a subject comprising administering an effective amount of a radiopharmaceutical to the subject, and imaging cancer tissue using positron emission tomography, wherein the radiopharmaceutical is a compound of the formula (XI),

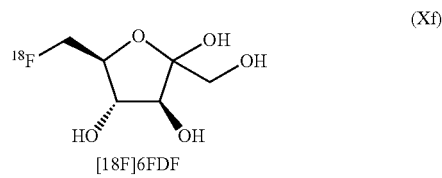 [SMILES: OCC1(O)O[C@H](C[18F])[C@@H](O)[C@@H]1O]

and is capable of being retained within cancer tissue sufficient to emit positrons for detection by positron emission tomography.

4. The method of claim 3, wherein the cancer is selected from a cancer of the brain, lung, breast, pancreas, kidney, colon, rectum, ovary, prostate, head, neck, thyroid, bladder, bone, endometrium, testicular cancer, gastric cancer, or neuroblastoma.

5. A method for monitoring cancer in a subject comprising:
   administering an effective amount of a radiopharmaceutical to a subject undergoing medical treatment for cancer;
   imaging cancer tissue using positron emission tomography; and comparing the quantity or distribution of the radiopharmaceutical present in the subject with a control quantity or distribution indicative of the effectiveness of the medical treatment, wherein the radiopharmaceutical is a compound of the formula (XI),

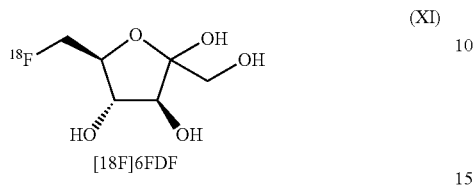

[18F]6FDF
(XI)

and is capable of being retained within cancer tissue sufficient to emit positrons for detection by positron emission tomography.

6. The method of claim 5, wherein the cancer is selected from a cancer of the brain, lung, breast, pancreas, kidney, colon, rectum, ovary, or prostate.

* * * * *

UNITED STATES PATENT AND TRADEMARK OFFICE
CERTIFICATE OF CORRECTION

PATENT NO. : 8,501,154 B2
APPLICATION NO. : 13/622599
DATED : August 6, 2013
INVENTOR(S) : Chris Cheeseman et al.

Page 1 of 1

It is certified that error appears in the above-identified patent and that said Letters Patent is hereby corrected as shown below:

In the Claims

Col. 22, Line 6-34, claim 1 should read

1. A method of preparing the radiopharmaceutical of formula:

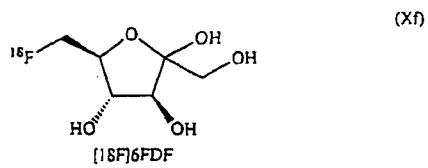

comprising reacting the compound of formula (X)

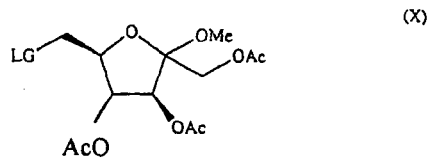

with a radioactive fluorinated complex to displace the leaving group to yield the radiopharmaceutical of formula (XI), wherein LG represents a leaving group, and wherein the leaving group is a trifluoromethane-sulfonate (triflate), chloride, bromide, iodide, 4-nitro-phenylsulfonate (nosylate), 4-methylphenylsulfonate (tosylate), or phenylsulfonate.

Signed and Sealed this
Twenty-ninth Day of October, 2013

Teresa Stanek Rea
*Deputy Director of the United States Patent and Trademark Office*